(12) United States Patent  (10) Patent No.: US 9,069,768 B1
Sampson  (45) Date of Patent: Jun. 30, 2015

(54) METHOD AND SYSTEM FOR CREATING SUBGROUPS OF DOCUMENTS USING OPTICAL CHARACTER RECOGNITION DATA

(71) Applicant: EMC Corporation, Hopkinton, MA (US)

(72) Inventor: Steven Sampson, Paris (FR)

(73) Assignee: EMC CORPORATION, Hopkinton, MA (US)

( * ) Notice: Subject to any disclaimer, the term of this patent is extended or adjusted under 35 U.S.C. 154(b) by 140 days.

(21) Appl. No.: 13/855,906

(22) Filed: Apr. 3, 2013

Related U.S. Application Data

(63) Continuation-in-part of application No. 13/432,139, filed on Mar. 28, 2012, now Pat. No. 8,595,235.

(51) Int. Cl.
*G06F 17/30* (2006.01)

(52) U.S. Cl.
CPC .... *G06F 17/30011* (2013.01); *G06F 17/30705* (2013.01); *G06F 17/30598* (2013.01)

(58) Field of Classification Search
CPC .................. G06F 17/30705; G06F 17/30722; G06F 17/30598
USPC .......................................... 707/737, 749, 758
See application file for complete search history.

(56) References Cited

U.S. PATENT DOCUMENTS

| | | | | |
|---|---|---|---|---|
| 5,857,179 | A * | 1/1999 | Vaithyanathan et al. | 707/999.002 |
| 5,987,460 | A * | 11/1999 | Niwa et al. | 707/999.004 |
| 7,213,205 | B1 | 5/2007 | Miwa et al | |
| 8,032,551 | B2 * | 10/2011 | Schneider | 707/770 |
| 8,180,781 | B2 | 5/2012 | Hiraoka | |
| 8,229,956 | B2 | 7/2012 | Ikeda et al. | |
| 8,386,264 | B2 * | 2/2013 | Hori et al. | 704/275 |
| 8,452,132 | B2 * | 5/2013 | Isaev et al. | 382/309 |
| 8,788,701 | B1 * | 7/2014 | Byrnes et al. | 709/238 |
| 8,819,023 | B1 * | 8/2014 | Wang et al. | 707/738 |
| 2002/0059281 | A1 | 5/2002 | Watanabe et al. | |
| 2002/0161753 | A1 * | 10/2002 | Inaba et al. | 707/3 |
| 2004/0140956 | A1 | 7/2004 | Kushler et al. | |
| 2005/0071365 | A1 * | 3/2005 | Hou et al. | 707/102 |
| 2005/0210056 | A1 | 9/2005 | Pomerantz et al. | |
| 2006/0288029 | A1 * | 12/2006 | Murakami et al. | 707/101 |
| 2007/0083808 | A1 | 4/2007 | Setlur et al. | |
| 2008/0065618 | A1 * | 3/2008 | Maluf | 707/5 |
| 2009/0076797 | A1 | 3/2009 | Yu | |
| 2009/0300007 | A1 | 12/2009 | Hiraoka | |

(Continued)

*Primary Examiner* — Phong Nguyen
(74) *Attorney, Agent, or Firm* — Dergosits & Noah LLP; Todd A. Noah

(57) ABSTRACT

Creating subgroups of documents using optical character recognition data is described. A matrix is created for words included in documents. Each column-row combination in the matrix indicates whether a corresponding word that is associated with the column-row combination is included in a corresponding document that is associated with the column-row combination. Distances are identified between pairs of the words. Each distance is based on a number of the documents that differ in including a corresponding pair of the words. Word clusters are created. Each word cluster includes pairs of words associated with a corresponding distance less than a distance threshold. Sets of word clusters are created. A set of word clusters includes word clusters that are not associated with any of the documents associated with other word clusters in the set. Subgroups of the digitized documents are created based on a set of word clusters with a highest word score.

20 Claims, 18 Drawing Sheets

(56) References Cited

U.S. PATENT DOCUMENTS

| | | | |
|---|---|---|---|
| 2010/0121642 A1* | 5/2010 | Hori et al. | 704/254 |
| 2010/0215272 A1* | 8/2010 | Isaev et al. | 382/182 |
| 2010/0287173 A1* | 11/2010 | Schneider | 707/759 |
| 2012/0072859 A1 | 3/2012 | Wang et al. | |
| 2012/0330977 A1 | 12/2012 | Inagaki | |
| 2013/0013612 A1* | 1/2013 | Fittges et al. | 707/739 |
| 2013/0021344 A1 | 1/2013 | Wang et al. | |
| 2013/0054595 A1* | 2/2013 | Isaev et al. | 707/736 |
| 2013/0204885 A1* | 8/2013 | Clinchant et al. | 707/756 |

* cited by examiner

402 → 406 ↓
         408 ↓  INVOICE: 123
404 ↓         ↓
         DATE: January 19, 2012

Peter's Electric
123 Main St.
San Francisco, CA 94111
Phone 415-987-6543
TO:                                    SHIP TO:

Tech Racing                            Tech Racing
1 Wall St.                             1 Wall St.
New York, NY 10005                     New York, NY 10005

| Sales Rep. | P.O. | Ship Date | Ship Via | FOB | Terms |
|---|---|---|---|---|---|
| Ben Lin | 87 | 1/3/12 | FedEx | | |

| Quantity | Description | Unit Price | Total |
|---|---|---|---|
| 1 | Geissler tube | $5.00 | $5.00 |
| 2 | Sonic reactor core | $100.00 | $200.00 |
| 2 | Flux Capacitor with auto shift | $45.00 | $90.00 |
| | 410 | | |
| | TOTAL | | $295.00 |

Make all checks payable to Peter 's Electric
THANK YOU FOR YOUR BUSINESS!

Peter's Electric                              INVOICE
123 Main St.
San Francisco, CA 94111
Phone 415-987-6543                    506
↓

INVOICE 123
508 → DATE: 2/5/2012

TO:                        FOR:
Tech Racing             Patriot Towers
1 Wall St.               P.O. # 12
New York, NY 10005

| DESCRIPTION | HOURS | RATE | AMOUNT |
|---|---|---|---|
| Install 45' copper line | 14 | $90.00 | $1260.00 |
| Remove extg fountain | 5 | $50 | $250.00 |
| Install underground tank | 10 | $80 | $800.00 |
|  |  |  |  |
|  |  |  |  |
|  |  |  |  |
|  |  |  |  |
|  |  |  |  |
|  |  |  |  |
|  |  |  |  |
|  |  |  |  |
|  |  | TOTAL | $2310.00 |

Total due in 15 days. Overdue accounts subject to a service charge of 1% per month. ↑
510

FIG. 5

602 → Peter's Electric
123 Main St.
San Francisco, CA 94111
Phone 415-987-6543

604 → INVOICE

606 → INVOICE 123
608 → DATE: 3/8/2012

TO:
Tech Racing
1 Wall St.
New York, NY 10005

FOR:
Shuttle
P.O. # 88

| DESCRIPTION | HOURS | RATE | AMOUNT |
|---|---|---|---|
| Install return air duct | 10 | $100.00 | $1000.00 |
| Paint exterior | 5 | $50 | $250.00 |
| Adjust flow pressure | 1 | $80 | $80.00 |
|  |  |  |  |
|  |  |  |  |
|  |  |  |  |
|  |  |  |  |
|  |  |  |  |
|  |  |  |  |
|  |  |  |  |
|  |  |  |  |
|  |  |  |  |
|  |  | TOTAL | $1330.00 |

Total due in 15 days. Overdue accounts subject to a service charge of 1% per month.

|  |  |  |  |  |  |
|---|---|---|---|---|---|
|  |  |  |  | INVOICE: | 123 |
| 1104 |  |  |  | DATE: January 19, 2012 | |
| 1106 → Peter's Electric<br>1108 — 123 Main St.<br>San Francisco, CA 94111<br>1110 Phone 415-987-6543 | | | | | |
| TO:<br>Tech Racing<br>1 Wall St.<br>New York, NY 10005<br>1114 → Phone 212-345-6789 | | | SHIP TO:<br>Tech Racing<br>1 Wall St.<br>New York, NY 10005 | | |

1112

| Sales Rep. | P.O. | Ship Date | Ship Via | FOB | Terms |
|---|---|---|---|---|---|
| Ben Lin | 87 | 1/3/12 | FedEx | | |

| Quantity | Description | Unit Price | Total |
|---|---|---|---|
| 1 | Geissler tube | $5.00 | $5.00 |
| 2 | Sonic reactor core | $100.00 | $200.00 |
| 2 | Flux Capacitor with auto shift | $45.00 | $90.00 |
|  | TOTAL | | $295.00 |

Make all checks payable to Peter's Electric
THANK YOU FOR YOUR BUSINESS!

Peter's Electric
123 Main Street
San Francisco, CA 94111

Branch: Boston MA Service - 0623

Bill To:
Tech Racing
987 Main St.
Hopkinton, MA 01748

Services Site:
See Locations listed below

Services Performed: For Period from 01-MAR-2010 to 31-MAR-2010
Locations included in your Agreement

| Tech Racing 987 Main St. | HOPKINTON, MA | USA | 01748-2205 |
| Tech Racing 987 Main St. | HOPKINTON, MA | USA | 01748-2209 |
|  | FRANKLIN, MA | USA | 02038-2531 |
| Tech Racing 987 Main St. | HOPKINTON, MA | USA | 01748-2209 |
| Tech Racing 987 Main St. | HOPKINTON, MA | USA | 01748-2209 |

| Sub Total | $20,386.00 |
| Taxes | $0.00 |
| Total Amount Due | USD| $20,386.00 |

1604

Direct Billing Inquiries: (855) 635-1328

Terms: if any invoice is not paid in full upon receipt, the Customer hereby agrees to pay interest at a rate of 1.5% per month (18% annually) upon the unpaid portion of the invoice. If action or suit in brought by Johnson Controls, Inc. to collect any amount due or owing under this bill, Customer agrees to pay all costs of collection including attorney's fees.

We hereby certify that these goods are produced in compliance with all applicable requirements of sections 6, 7 and 12 of the Fair Labor Standards Act of 1936, as amended, and of regulations and orders of the Administrator of the Wages and Hour Division issued under section 14 thereof.

4100217993

Page 1 of 2

1602

4100217992

Peter's Electric
123 Main Street
San Francisco, CA 94111

Branch: Boston MA Service - 0623

1602

Please reference our Invoice Number and amount with your payment and send ONLY to the address on this invoice Payment Terms: Net Cash-Due Upon Receipt    Remit Payment To:
Direct Billing Inquiries
To Service Department (855) 635-1328          Peter's Electric
To Remit Via Credit Card:                     123 Main Street
Call the Phone Number listed above.           San Francisco, CA 94111

INVOICE #:    123

AMOUNT DUE:   $20,386.00

1606

Page 2 of 2

| Document 1 | Document 2 | Document 3 | Document 4 | Document 5 |        |
|------------|------------|------------|------------|------------|--------|
| X          | X          | X          | X          | X          | word 1 |
| X          | X          | X          | X          | X          | word 2 |
| X          | X          | X          |            | X          | word 3 |
| X          |            | X          |            | X          | word 4 |
| X          |            | X          |            | X          | word 5 |
|            | X          |            | X          |            | word 6 |
|            | X          |            | X          |            | word 7 |
| X          | X          |            |            |            | word 8 |
| X          |            | X          |            |            | word 9 |

|        | word 1 | word 2 | word 3 | word 4 | word 5 | word 6 | word 7 | word 8 | word 9 |
|--------|--------|--------|--------|--------|--------|--------|--------|--------|--------|
| word 1 |        | 0      | 1      | 2      | 2      | 3      | 3      | 3      | 3      |
| word 2 | 0      |        | 1      | 2      | 2      | 3      | 3      | 3      | 3      |
| word 3 | 1      | 1      |        | 1      | 1      | 4      | 4      | 2      | 2      |
| word 4 | 2      | 2      | 1      |        | 0      | 5      | 5      | 3      | 1      |
| word 5 | 2      | 2      | 1      | 0      |        | 5      | 5      | 3      | 1      |
| word 6 | 3      | 3      | 4      | 5      | 5      |        | 0      | 2      | 4      |
| word 7 | 3      | 3      | 4      | 5      | 5      | 0      |        | 2      | 4      |
| word 8 | 3      | 3      | 2      | 3      | 3      | 2      | 2      |        | 2      |
| word 9 | 3      | 3      | 2      | 1      | 1      | 4      | 4      | 2      |        |

METHOD AND SYSTEM FOR CREATING SUBGROUPS OF DOCUMENTS USING OPTICAL CHARACTER RECOGNITION DATA

CROSS REFERENCE TO RELATED APPLICATIONS

This application is a continuation-in-part of U.S. patent application Ser. No. 13/432,139, filed Mar. 28, 2012, the entire contents of which are incorporated herein by reference.

BACKGROUND

For many organizations, information can be the foundation for competitive differentiation, from faster processing time and reduced operating costs to quicker access to information and ensured compliance. The sheer volume and complexity of information can thwart productivity, waste time and resources, and strain the information technology infrastructure that supports the information. A key to utilizing information successfully is the ability to efficiently capture and manage large volumes of information from disparate sources. Business critical information arrives in many forms, including paper and fax. Transforming the information into intelligent content can feed enterprise applications such as enterprise content management, enterprise resource planning, customer relationship management, and other information systems. Grouping and classifying paper documents that have been scanned can be very difficult because of optical character recognition (OCR) errors, differences in text, differences in graphics, noise, stray marks, rotations, skewing, handwriting, and so forth.

BRIEF DESCRIPTION OF THE DRAWINGS

Advantages of the subject matter claimed will become apparent to those skilled in the art upon reading this description in conjunction with the accompanying drawings, in which like reference numerals have been used to designate like elements, and in which:

FIG. 4 illustrates another example of a document for grouping and creating document classes, under an embodiment;

FIG. 5 illustrates yet another example of a document for grouping and creating document classes, under an embodiment;

FIG. 6 illustrates a further example of a document for creating subgroups of documents using optical character recognition data, under an embodiment;

FIG. 11 illustrates the grid being applied to another example document for grouping and creating document classes, under an embodiment;

FIG. 16 illustrates an example of two documents that were grouped together for creating subgroups of documents using optical character recognition data, under an embodiment;

FIG. 17 illustrates an example matrix for a set of documents that have common words for creating subgroups of documents using optical character recognition data, under an embodiment;

FIG. 18 illustrates a distance table for a set of documents that have common words for creating subgroups of documents using optical character recognition data, under an embodiment.

DETAILED DESCRIPTION

Figure 1:
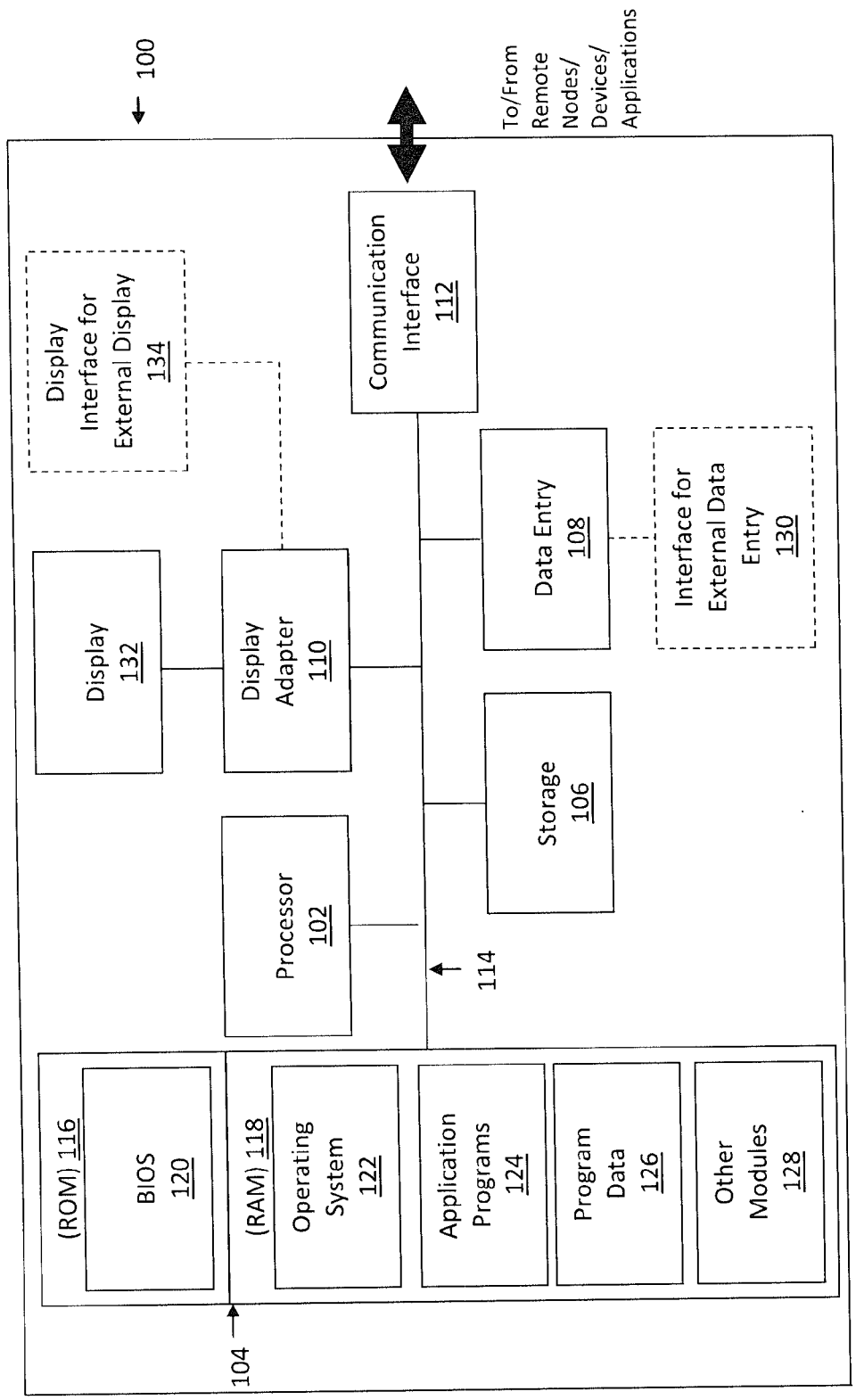
FIG. 1 is a block diagram illustrating an example hardware device in which the subject matter may be implemented.

Documents that contain a substantial number of words in common are grouped together. These documents are generally closely related, such as different pages from the same invoice. To get higher accuracy recognition, document management should subdivide these kinds of pages and treat them semi-independently, as there will be common parts of the documents, such that treating the common parts in the same way may be desirable. In particular, document management should automatically find the position of fields in each subgroup, such as the field for the amount due in an invoice.

Embodiments herein enable creating subgroups of documents using optical character recognition data. A matrix is created for words included in documents. In a very simple example, a matrix with columns for 5 documents and rows for 9 words is created for a class of invoice documents. Each column-row combination in the matrix indicates whether a corresponding word that is associated with the column-row combination is included in a corresponding document that is associated with the column-row combination. In a very simple example, the combination of the first column and the first row indicates that document 1 includes word 1. Distances are identified for pairs of the words, wherein each distance is based on a number of the documents that differ in including a corresponding pair of the words. In a very simple example, the distance between word 2 and word 3 is 1 because all of the 5 documents include word 2 and all of the 5 documents except 1, document 4, include word 3. Word clusters are created, wherein each word cluster includes pairs of words associated with a corresponding distance less than a distance threshold. In a very simple example, cluster 2 is created to include word 4, word 5, and word 9 because the distances between each of the words in cluster 2 are less than a distance threshold of 2. Sets of word clusters are created, wherein a set of word clusters includes word clusters that are not associated with any of the documents associated with other word clusters in the set. In a very simple example, cluster set 2 is created to include cluster 2 and cluster 3 because documents 1, 3, and 5 that are associated with cluster 2 are not included in the documents 2 and 4 that are associated with cluster 3. Subgroups of the digitized documents are created based on a set of word clusters with a highest word score. In a very simple example, the documents are divided into 2 subgroups, subgroup 1 for documents 1, 3, and 5, and subgroup 2 for documents 2 and 4 because cluster set 2 includes 5 words, which is more than the number of words included in cluster set 1 or cluster set 3. As a result, documents 1, 3, and 5 are grouped together as first pages of invoices while documents 2 and 4 are grouped together as last pages of multi-paged invoices. This document management distinguishes pages by their content rather than their overall "look," resulting in a better subdivision of documents and higher recognition accuracy.

Prior to describing the subject matter in detail, an exemplary hardware device in which the subject matter may be implemented shall first be described. Those of ordinary skill in the art will appreciate that the elements illustrated in FIG. 1 may vary depending on the system implementation. With reference to FIG. 1, an exemplary system for implementing the subject matter disclosed herein includes a hardware device 100, including a processing unit 102, memory 104, storage 106, data entry module 108, display adapter 110, communication interface 112, and a bus 114 that couples elements 104-112 to the processing unit 102.

The bus 114 may comprise any type of bus architecture. Examples include a memory bus, a peripheral bus, a local bus, etc. The processing unit 102 is an instruction execution machine, apparatus, or device and may comprise a microprocessor, a digital signal processor, a graphics processing unit, an application specific integrated circuit (ASIC), a field programmable gate array (FPGA), etc. The processing unit 102 may be configured to execute program instructions stored in memory 104 and/or storage 106 and/or received via data entry module 108.

The memory 104 may include read only memory (ROM) 116 and random access memory (RAM) 118. Memory 104 may be configured to store program instructions and data during operation of device 100. In various embodiments, memory 104 may include any of a variety of memory technologies such as static random access memory (SRAM) or dynamic RAM (DRAM), including variants such as dual data rate synchronous DRAM (DDR SDRAM), error correcting code synchronous DRAM (ECC SDRAM), or RAMBUS DRAM (RDRAM), for example. Memory 104 may also include nonvolatile memory technologies such as nonvolatile flash RAM (NVRAM) or ROM. In some embodiments, it is contemplated that memory 104 may include a combination of technologies such as the foregoing, as well as other technologies not specifically mentioned. When the subject matter is implemented in a computer system, a basic input/output system (BIOS) 120, containing the basic routines that help to transfer information between elements within the computer system, such as during start-up, is stored in ROM 116.

The storage 106 may include a flash memory data storage device for reading from and writing to flash memory, a hard disk drive for reading from and writing to a hard disk, a magnetic disk drive for reading from or writing to a removable magnetic disk, and/or an optical disk drive for reading from or writing to a removable optical disk such as a CD ROM, DVD or other optical media. The drives and their associated computer-readable media provide nonvolatile storage of computer readable instructions, data structures, program modules and other data for the hardware device 100.

It is noted that the methods described herein can be embodied in executable instructions stored in a computer readable medium for use by or in connection with an instruction execution machine, apparatus, or device, such as a computer-based or processor-containing machine, apparatus, or device. It will be appreciated by those skilled in the art that for some embodiments, other types of computer readable media may be used which can store data that is accessible by a computer, such as magnetic cassettes, flash memory cards, digital video disks, Bernoulli cartridges, RAM, ROM, and the like may also be used in the exemplary operating environment. As used here, a "computer-readable medium" can include one or more of any suitable media for storing the executable instructions of a computer program in one or more of an electronic, magnetic, optical, and electromagnetic format, such that the instruction execution machine, system, apparatus, or device can read (or fetch) the instructions from the computer readable medium and execute the instructions for carrying out the described methods. A non-exhaustive list of conventional exemplary computer readable medium includes: a portable computer diskette; a RAM; a ROM; an erasable programmable read only memory (EPROM or flash memory); optical storage devices, including a portable compact disc (CD), a portable digital video disc (DVD), a high definition DVD (HD-DVD™), a BLU-RAY disc; and the like.

A number of program modules may be stored on the storage 106, ROM 116 or RAM 118, including an operating system 122, one or more applications programs 124, program data 126, and other program modules 128. A user may enter commands and information into the hardware device 100 through data entry module 108. Data entry module 108 may include mechanisms such as a keyboard, a touch screen, a pointing device, etc. Other external input devices (not shown) are connected to the hardware device 100 via external data entry interface 130. By way of example and not limitation, external input devices may include a microphone, joystick, game pad, satellite dish, scanner, or the like. In some embodiments, external input devices may include video or audio input devices such as a video camera, a still camera, etc. Data entry module 108 may be configured to receive input from one or more users of device 100 and to deliver such input to processing unit 102 and/or memory 104 via bus 114.

A display 132 is also connected to the bus 114 via display adapter 110. Display 132 may be configured to display output of device 100 to one or more users. In some embodiments, a given device such as a touch screen, for example, may function as both data entry module 108 and display 132. External display devices may also be connected to the bus 114 via external display interface 134. Other peripheral output devices, not shown, such as speakers and printers, may be connected to the hardware device 100.

The hardware device 100 may operate in a networked environment using logical connections to one or more remote nodes (not shown) via communication interface 112. The remote node may be another computer, a server, a router, a peer device or other common network node, and typically includes many or all of the elements described above relative to the hardware device 100. The communication interface 112 may interface with a wireless network and/or a wired network. Examples of wireless networks include, for example, a BLUETOOTH network, a wireless personal area network, a wireless 802.11 local area network (LAN), and/or wireless telephony network (e.g., a cellular, PCS, or GSM network). Examples of wired networks include, for example, a LAN, a fiber optic network, a wired personal area network, a telephony network, and/or a wide area network (WAN). Such networking environments are commonplace in intranets, the Internet, offices, enterprise-wide computer networks and the like. In some embodiments, communication interface 112 may include logic configured to support direct memory access (DMA) transfers between memory 104 and other devices.

In a networked environment, program modules depicted relative to the hardware device 100, or portions thereof, may be stored in a remote storage device, such as, for example, on a server. It will be appreciated that other hardware and/or software to establish a communications link between the hardware device 100 and other devices may be used.

It should be understood that the arrangement of hardware device 100 illustrated in FIG. 1 is but one possible implementation and that other arrangements are possible. It should also be understood that the various system components (and means) defined by the claims, described below, and illustrated in the various block diagrams represent logical components that are configured to perform the functionality described herein. For example, one or more of these system components (and means) can be realized, in whole or in part, by at least some of the components illustrated in the arrangement of hardware device 100. In addition, while at least one of these components are implemented at least partially as an electronic hardware component, and therefore constitutes a machine, the other components may be implemented in software, hardware, or a combination of software and hardware. More particularly, at least one component defined by the claims is implemented at least partially as an electronic hardware component, such as an instruction execution machine (e.g., a processor-based or processor-containing machine) and/or as specialized circuits or circuitry (e.g., discrete logic gates interconnected to perform a specialized function), such as those illustrated in FIG. 1. Other components may be implemented in software, hardware, or a combination of software and hardware. Moreover, some or all of these other components may be combined, some may be omitted altogether, and additional components can be added while still achieving the functionality described herein. Thus, the subject matter described herein can be embodied in many different variations, and all such variations are contemplated to be within the scope of what is claimed.

In the description that follows, the subject matter will be described with reference to acts and symbolic representations of operations that are performed by one or more devices, unless indicated otherwise. As such, it will be understood that such acts and operations, which are at times referred to as being computer-executed, include the manipulation by the processing unit of data in a structured form. This manipulation transforms the data or maintains it at locations in the memory system of the computer, which reconfigures or otherwise alters the operation of the device in a manner well understood by those skilled in the art. The data structures where data is maintained are physical locations of the memory that have particular properties defined by the format of the data. However, while the subject matter is being described in the foregoing context, it is not meant to be limiting as those of skill in the art will appreciate that various of the acts and operation described hereinafter may also be implemented in hardware.

To facilitate an understanding of the subject matter described below, many aspects are described in terms of sequences of actions. At least one of these aspects defined by the claims is performed by an electronic hardware component. For example, it will be recognized that the various actions can be performed by specialized circuits or circuitry, by program instructions being executed by one or more processors, or by a combination of both. The description herein of any sequence of actions is not intended to imply that the specific order described for performing that sequence must be followed. All methods described herein can be performed in any suitable order unless otherwise indicated herein or otherwise clearly contradicted by context. In an embodiment, the computer system 100 includes one or more methods for creating subgroups of documents using optical character recognition data.

Figure 2:
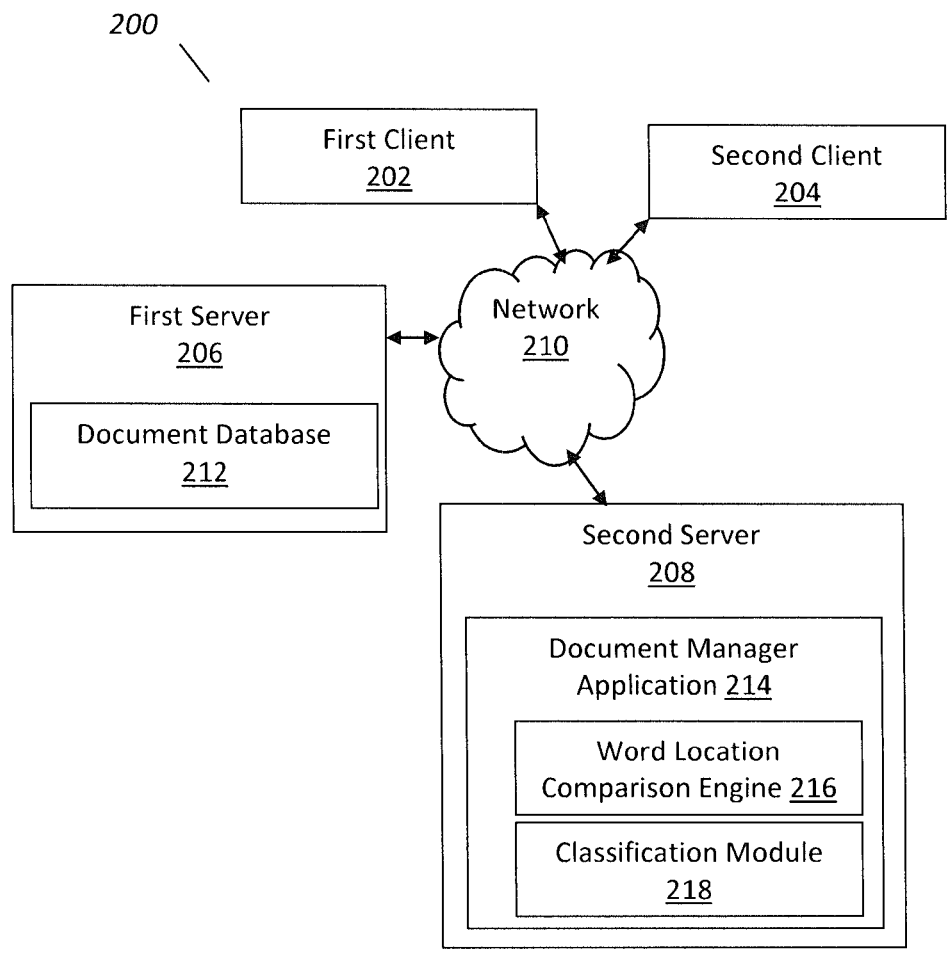
FIG. 2 illustrates a block diagram of an example system for creating subgroups of documents using optical character recognition data, under an embodiment.

FIG. 2 illustrates a block diagram of a system that implements creating subgroups of documents using optical character recognition data, under an embodiment. As shown in FIG. 2, system 200 may illustrate a cloud computing environment in which data, applications, services, and other resources are stored and delivered through shared data-centers and appear as a single point of access for the users. The system 200 may also represent any other type of distributed computer network environment in which servers control the storage and distribution of resources and services for different client users.

In an embodiment, the system 200 represents a cloud computing system that includes a first client 202 and a second client 204; and a first server 206 and a second server 208 that are provided by a hosting company. The clients 202-204 and the servers 206-208 communicate via a network 210. An enterprise uses the clients 202-204 to execute an enterprise application via the servers 206-208. The first server 206 includes a document database 212. The second server 208 includes a document manager application 214, which includes a word location comparison engine 216 and a classification module 218. The second server 208 executes the document manager application 214 to classify documents, create templates for each class of documents, and create subgroups of documents using optical character recognition data. Although FIG. 2 depicts the document database 212 residing in the first server 206 and the document manager application 214 residing in the second server 208, any portion of the document database 212 may reside in the second server 208 and any portion of the document manager application 214 may reside in the first server 206. Although FIG. 2 depicts the system 200 with two clients 202-204, two servers 206-208, one network 210, one document database 212, one document manager application 214, one word location comparison engine 216, and one classification module 218, the system 200 may include any number of clients 202-204, servers 206-208, networks 210, document databases 212, document manager applications 214, word location comparison engines 216, and classification modules 218. The clients 202-204 and the servers 206-208 may each be substantially similar to the system 100 depicted in FIG. 1.

In brief, the document manager application 214 receives as input a set of documents that may be used to train the document manager applications 214. The document manager application 214 outputs a set of document classes and a set of document templates. Each document template is associated with a document class. The set of document classes and templates are processed by the classification module 218. The classification module 218 receives as input a document to be classified. The classification module 218 outputs a classification result. The classification result may specify the document class in which the document should be classified.

More particularly, during a training step the location comparison engine 218 compares a document, such as a first document, in the set of documents with another document, such as a second document, in the set of documents. If the comparison indicates that the first and second documents are similar, the document manager application 214 may create a document class and an associated template for classifying documents similar to the first and second documents. If the comparison indicates that the first and second documents are different, the document manager application 214 may create a first document class and an associated first template for classifying documents similar to the first document, and a second document class and an associated second template for classifying documents similar to the second document.

While the training may be automated, this is not, however, always the case. The training of the document manager application 214 may include manual techniques. Automated training may be supplemented with manual training. For example, training may include the involvement of a user, such as an administrator. In other words, it is possible to train the document manager application 214 using a human because automatic learning is not the only way to create document classes and templates. A user may supervise the training and make appropriate adjustments as desired.

During a classification step, the classification module 218 can be used to classify a document into a particular document class using the templates. For example, the classification module 218 can compare the document to be classified against the document templates. Based on the comparison between the document and a document template, the classification module 218 may classify the document may be classified into a document class associated with a document template.

The classification module 218 uses textual content present on a page to compare two images, such as documents or document images, to determine if they belong in the same class. The classification module 218 may use fuzzy textual matching and spatial relations of words to determine whether two documents belong in the same class. Structured and semi-structured documents may have certain patterns that are text-based such as "Total," "Invoice #," and so forth, that appear in the same relative position in each document of the same class. The classification module 218 may learn these common text patterns and their relative locations and apply this learning on production document images to provide improved grouping and classification methods. This learnt information can be leveraged in extracting business data.

The document manager application 214 can capture data from scanned images including structured, semi-structured documents, such as invoices and forms. Classification is the process of the classification module 218 deciding whether an object belongs in a particular class from a set of classes. In order to classify, the classification module 218 can provide a set of templates defining each object class. A training step may take a set of images and creates a set of classes from these images. The images may be images of documents, such as physical documents that have been scanned via a scanner and output as optical character recognition (OCR) data, in the form of scanned or digitized documents. This training step may be a manual process or an automated process. The classification module 218 then compares an image with each of the classes and decides in which class or classes the image belongs. If the image belongs to only one class, the image may be considered classified. Otherwise, the image may either be over-classified or not classified at all.

There may be an automated training step, a classification step, or both, which use a comparison function (which may be referred to as a distance function) to determine whether an image is "close" to another image or template. The training and classification steps may use this comparison function. There may be a "training" comparison function that compares two images, and a "classification" function that compares an image and a reference set of keywords.

In structured and semi-structured documents, words sometimes consistently appear in the same place relative to each other. For example, the word "x" appears a distance of 20 pixels to the right and 40 pixels higher from a word "y" on a first document. If the word location comparison engine 216 identifies the word "x" on a second document about 20 pixels to the right and 40 pixels higher from the word "y" on the second document, the word "x" and the word "y" are considered to be in the same relative position, and hence increases the probability that these two documents are from the same class. The word location comparison engine 216 attempts to find the set of words that appear in the same place in two documents. If only a handful of words are in common, then the documents are unlikely to be the same type of document. However, if the word location comparison engine 216 finds 20 to 30 words all in the same place with respect to each other, the word location comparison engine 216 may determine that the documents are related.

Figure 3:
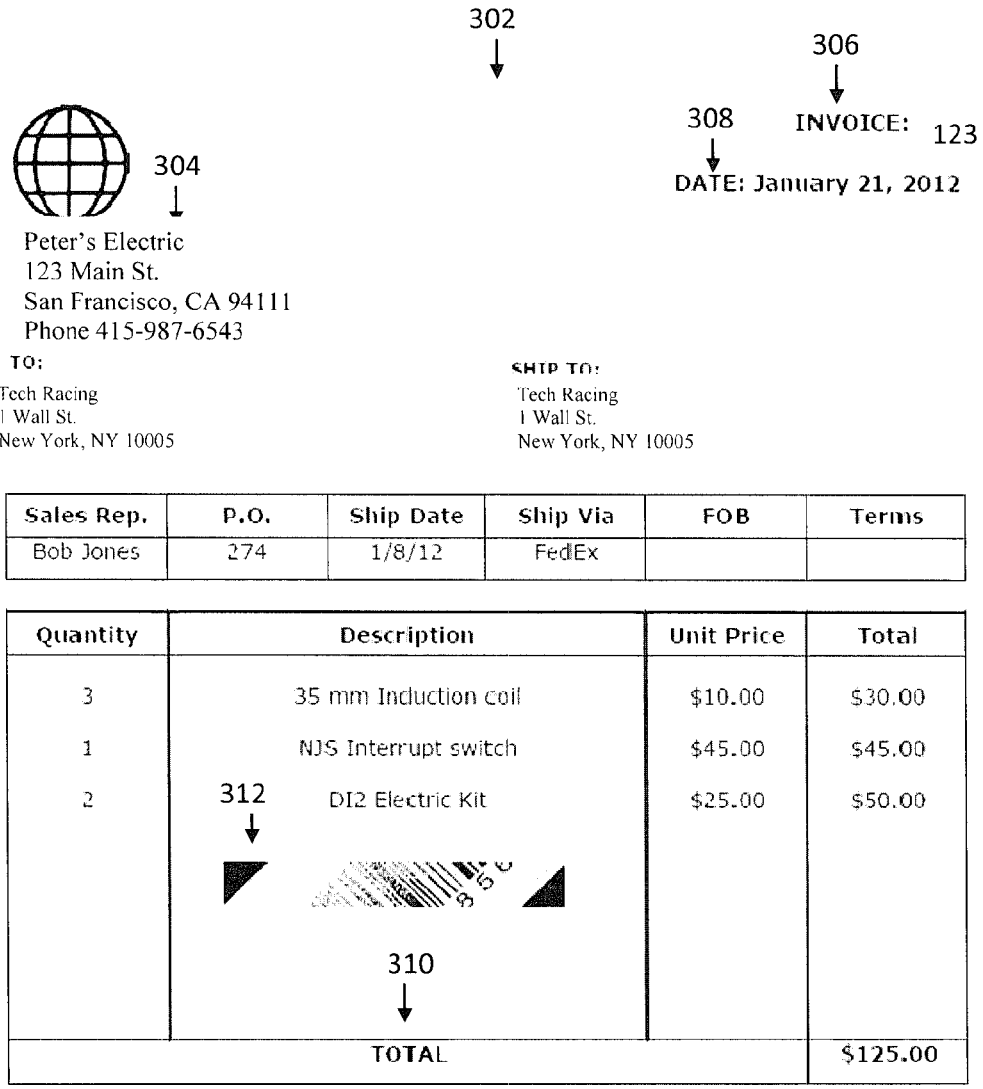
FIG. 3 illustrates an example of a document for grouping and creating document classes, under an embodiment.

As an example, FIG. 3, FIG. 4, and FIG. 5 each illustrate an image of a document or invoice. The two images 302 (FIG. 3) and 402 (FIG. 4) come from two documents that may be in the same class. The image 302 includes a word "Dresden" 304, a word "INVOICE" 306, a word "DATE" 308, and a word "TOTAL" 310. The image 402 includes a word "Dresden" 404 that corresponds to the word "Dresden" 304," a word "INVOICE" 406 that corresponds to the word "INVOICE" 306, a word "DATE" 408 that corresponds to the word "DATE" 308, and a word "TOTAL" 410 that corresponds to the word "TOTAL" 310. These are some examples of the types of words that may be identified by the word location comparison engine 216. The words Dresden," "INVOICE," "DATE," and "TOTAL," all appear in the same place on examples of the images 302 and 402 of the invoices. For example, the location of the word "INVOICE" 306 relative to the word "DATE" 308 in the image 302 is about the same as the location of the word "INVOICE" 406 relative to the word "DATE" 408 in the image 402.

The image 502 (FIG. 5) includes a word 'INVOICE" 502 and a word 'INVOICE" 504 that are the same as the word "INVOICE" 306, a word "DATE" 506 that is the same as the word "DATE" 308, and a word "TOTAL" 510 that is the same as the word "TOTAL" 310. In other words, the image 502 also has the words "INVOICE," "DATE," and "TOTAL." However, these words are in completely different relative positions. Because the data, such as the invoice number, appears to be offset with respect to the underlying form, these data may not be found as common between the two documents. For example, a location of the word 'INVOICE" 504 relative to the word "DATE" 508 in the image 502 is different from the location of the word INVOICE" 306 relative to the word "DATE" 308 in the image 302. Therefore, the word location comparison engine 216 is unlikely to determine that the documents for the images 302 and 502 are related.

FIG. 6 illustrates a further example of a document for creating subgroups of documents using optical character recognition data, under an embodiment. FIG. 6 will be referenced below in FIG. 9's discussion of word size.

Figure 7:
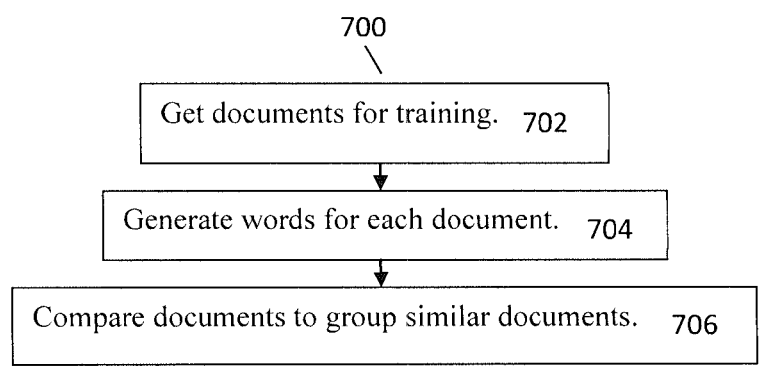
FIG. 7 illustrates a simplified flowchart for grouping and creating document classes, under an embodiment.

FIG. 7 illustrates a simplified flowchart for creating one or more classes based on a set of documents, under an embodiment. The documents may be referred to as training documents. The document manager application 214 receives or gets documents for training, act 702. The documents may be received from a scanner or other device capable of providing a digital image, digitized representation, or digital representation of physical document papers. The documents may be digitized documents, scanned documents, or digital representations of physical documents. Some specific examples of documents include invoices, tax forms, applications, insurance claims, purchase orders, checks, financial documents, mortgage documents, health care records, legal documents, and so forth. The documents may be from different vendors, suppliers, manufacturers, individuals, groups, companies, entities, and so forth. The received document data includes optical character recognition (OCR) data such as a set of characters with position information, confidence information, or both. The received document data may include a set of optical character recognition data sets, with each data set being associated with a document, and including a list of characters or words.

The word location comparison engine 216 generates a list of words for each document, act 704. A list of words includes one or more words from a document. Generating a list of words for a document may include a pretreatment process. A pretreatment process transforms optical character recognition data into data that is more suited to doing comparison calculations. For example, in some cases weighing certain differences between two documents to determine whether or not the documents should be in the same class may not be desirable. In a specific example, in some places on forms and invoices where a number might appear, the number is likely to vary, such as a "Total: $123.00" and "Total: $999.99," or "Nov. 24, 2011" versus "Oct. 19, 2012". Thus, a pretreatment technique may include altering digits to a predefined value, such as 0, to allow the word location comparison engine 216 to consider different numerical values between two documents to be the "same" value or to be considered as the same type of data. In order to facilitate the matching of numbers, the word location comparison engine 216 may change all digits to a predefined value, such as 0. A pretreatment process may include a first pretreatment sub-process to alter certain recognized characters, a second pretreatment sub-process to remove certain recognized characters, or both. The first pretreatment sub-process may include changing, altering, modifying, editing, or mapping recognized digits such as 0, 1, 2, 3, 4, 5, 6, 7, 8, or 9, to a predefined value, such as 0. For example, the word location comparison engine 216 may change the number "123" to become "000." The pretreatment step can be equivalent to changing the fuzzy text comparison function, which is discussed below, to treat all numbers the same. After altering the numerical values on the two documents to compare, the word location comparison engine 216 can match "999" and "123." Changing recognized digits to a predefined value is merely one example of a number matching algorithm. Other techniques include blocking, matching weights, and threshold of likelihood, which may be used instead or additionally. A pretreatment process may include mapping each numerical digit of a first number in a first document to a predefined value to alter the first number to a first altered number, and mapping each numerical digit of a second number, which may be different from the first number, in the second document to the predefined value to alter the second number to a second altered number, the same as the first altered number. A second pretreatment sub-process may include removing words having a single character, which may be noise from a scanning process or may be a graphic that is interpreted as a letter. One letter words may be removed, rejected, or flagged so that they are not considered because such words may be noise or stray marks on a document that may skew the scoring or results.

The classification module 218 compares the documents using generated word lists to group similar documents, act 706. The classification module 218 may incorporate a similarity function, which may be referred to as a distance function, which is an algorithm that makes, among other things, a set of word pairs, each word pair including a word from a first document and a word from a second document. The word location comparison engine 216 takes a pair of documents and returns a "distance," which can indicate whether or not the pair of documents are similar, and thus should be in the same class, or dissimilar, and thus should be in different classes. The classification module 218 may use the spatial relations of words to classify and group similar documents. A function referred to as a textual distance function takes as input two images, such as digitized documents or document images, and outputs a distance or score, which indicates whether or not the two documents are similar or dissimilar. The textual distance function may the form: "distance (first document, second document)."

More particularly, the word location comparison engine 216 may include a comparison function that takes optical character recognition data that may include a set of characters with position and confidence information from two images and finds a set of words that appear in both of the images in approximately the same relative position. Upon finding the set of common words, the set of common words is passed to a scoring function that takes into account a number and size of the common words. The score generated by the scoring function may be proportional to the number of common words, the size of the common words, or both. More words and bigger words can mean a higher score as compared to fewer and smaller words. If a score exceeds a threshold value, then the two associated images may be considered "in the same class."

Figure 8:
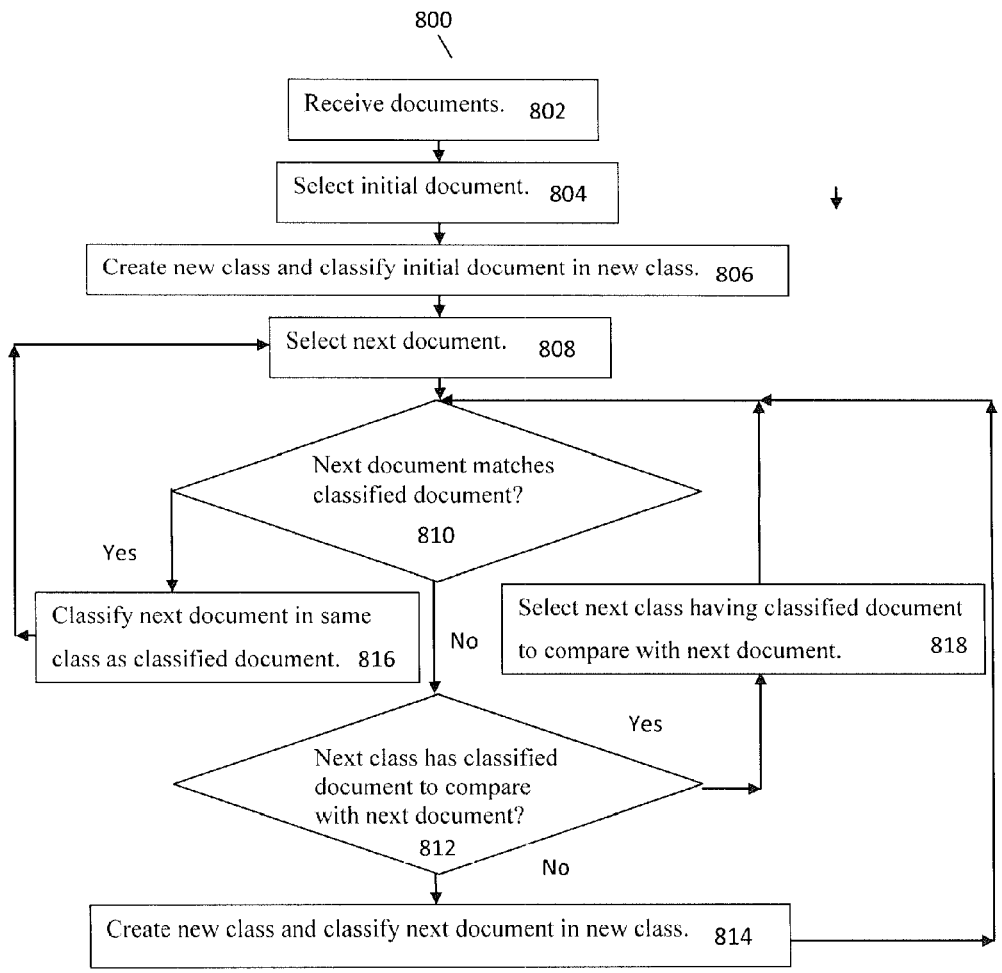
FIG. 8 illustrates a more detailed flowchart for grouping and creating document classes, under an embodiment.

FIG. 8 illustrates a more detailed flowchart for grouping and creating document classes, under an embodiment. The document manager application 214 receives a set of documents for creating the document classes, act 802. The classification module 218 selects an initial document from the document set, act 804. The classification module 218 creates a new class and classifies the initial document in the new class, the initial document now being a classified document, act 806.

The classification module 218 selects the next document from the document set, act 808. The selected document may be ordered or positioned in the document set after the now classified document. The selected document may be the next document in the document set immediately after the now classified document. However, the selected document may not be the document ordered immediately after the now classified document.

The classification module 218 compares the now classified document with the selected document, act 810. The classification module 218 determines whether there is a match between the classified document and the selected document, act 812.

If there is not a match, the classification module 218 determines whether there is another or a next class having a classified document to compare with the selected document, act 814. If there is no other class to compare, the classification module 218 creates a new class and classifies the selected document in the new class, the selected document now being a classified document, act 816. Assuming that there are remaining documents in the document set after classifying the selected document, the classification module 218 loops back to act 808 to select another document that will be compared.

However, if the classification module 218 determines that there is a match between the classified document and the selected document in act 810, the classification module 218 classifies the selected document in the same class as the classified document, act 816. Assuming there are remaining documents in the document set after the classifying, the classification module 218 loops back to act 808 to select another document. One or more counter variables can be used to track the remaining documents, the number of classes, the number of documents in each class, and so forth.

If the classification module 218 determines that there is a next or another class having a classified document to compare with the selected document in act 812, the classification module 218 selects the next class having the classified document to compare with the selected document, in act 818; and loops back to act 810 to perform the comparison.

As an example to further illustrate the flowchart 800, the classification module 218 receives a document set that has A1, B1, B2, A2, A3, C1, B3, C2, D1, and A4, in this order or sequence. The classification module 218 starts with no classes, and takes each document. Document A1 does not match any existing class because no classes exist yet, so the classification module 218 creates a new class A and adds the document A1 to the class A. Document B1 does not match class A, so the classification module 218 creates a new class B and puts the document B1 in class B. Document B2 does not match the class A, but matches the class B, so the classification module adds the document B2 to the class B, which now has the document B1 and the document B2. Document A2 matches the class A, so the classification module 218 adds the document A2 to the class A, which now has the document A1 and the document A2. Document A3 matches the class A, so the classification module 218 adds the document A3 to the class A, which now has the document A1, the document A2, and the document A3. Document C1 does not match the class A or the class B, so the classification module 218 creates a new class C and puts the document C1 in the class C. Document B3 does not match with the class A, but matches the class B, so the classification module 218 adds the document B3 to the class B, which now has the document B1, the document B2, and the document B3. Document C2 does not match the class A or the class B, but matches the class C, so the classification module 218 adds the document C2 to the class C, which now has the document C1 and the document C2. Document D1 does not match the class A or the class B or the class C, so the classification module 218 creates a new class D and puts the document D1 in the class D. Document A4 matches the class A, so the classification module 218 adds the document A4 to the class A, which now has the document A1, the document A2, the document A3, and the document A4. At the end of this process, the classification module 218 has creates 4 classes: the class A, which includes the document A1, the document A2, the document A3, and the document A4; the class B, which includes the document B1, the document B2, and the document B3; the class C, which includes the document C1 and the document C2; and the class D, which includes the document D1. The classification module 218 may filter for classes that are too small, containing only a few images, so the class size may be based on a customer-settable or user-configurable parameter.

Figure 9:
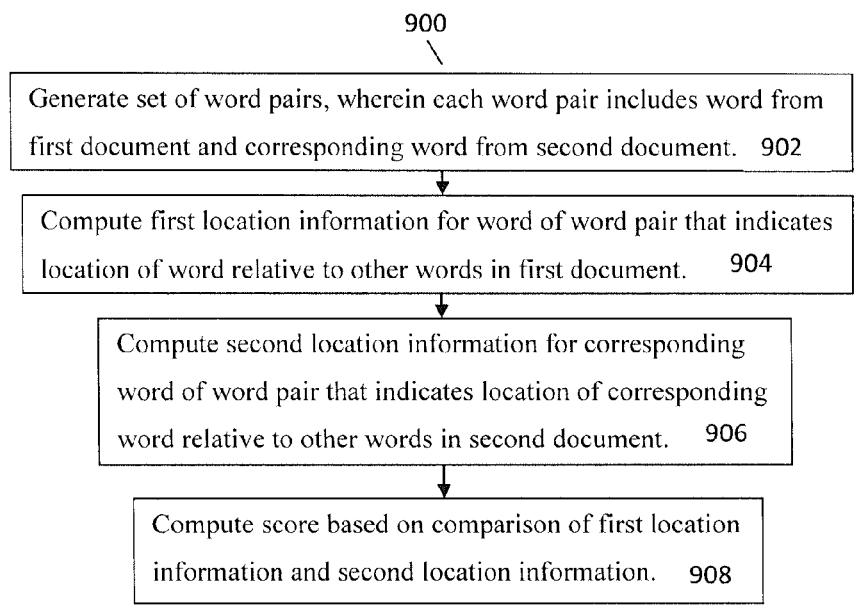
FIG. 9 illustrates a flowchart of a textual distance function used to compare documents, under an embodiment.

FIG. 9 illustrates a flowchart of a textual distance function used to compare documents, under an embodiment. The word location comparison engine 216 generates a set of word pairs, act 902. Each word pair includes a word from a first document of the set of documents and a corresponding word from a second document of the set of documents. There may be a first list of recognized words from a first document and a second list of recognized words from a second document. The word location comparison engine 216 can then take the two lists of words and create a list of the words from the one page or document that have approximately the same text and approximately the same size as the words on the other page or document. This results in a list of pairs of words, with one word from each page or document. A word can include any character, symbol, number, or any combination of characters, symbols, or numbers.

Identifying the words for a word pair may be based on any number of factors. The word location comparison engine 216 may use a first factor, a second factor, or both. The first factor may be based on calculating a value of a string metric between a first word from a first document and a second word from a second document. For example, if the value is below a threshold value, the first word may be included as a word in a word pair and the second word may be included as a corresponding word in the word pair. A string metric may measure an amount of difference between two words. The string metric may be a "Levenshtein distance," which is a means of getting a distance between two strings. A Levenshtein distance may determine whether a first word from a first document and a second word from a second document should be in a word pair, the first word being a word in the word pair and the second word being a corresponding word in the word pair. Other approximate string matching algorithms, fuzzy string searching, or edit distance metrics may instead or additionally be used, such as the length of the longest common subsequence, a Damerau-Levenshtein distance, or a Hamming distance. These string matching techniques can be used to compensate for mistakes that may be made by an optical character recognition engine. For example, optical character recognition engines may confuse "I" and "l," the upper case "I" and the lower case "L," respectively, or confuse "rn," the combination of the letters "r" and "n," with the letter "m." To compensate for such errors, the word location comparison engine 216 can use a fuzzy definition of "same."

The second factor may be based on calculating a size or area of the words. If an area occupied by a first word on a first document is about the same as an area occupied by a second word on a second document, the first word may be included as a word in a word pair and the second word may be included as a corresponding word in the word pair. Generally, it is undesirable to match two words of different sizes or consider them to be the "same" or corresponding to each other. In other words, it is desirable to match words having approximately the same size, such as font size. For example, the word "Invoice" may be the first and second words on a first and second document, respectively. On the first document, the word may be in a 12-point font size. On the second document, however, the word may be in a 48-point font size. The difference in size may indicate that the two words should not be considered as a pair. Thus, even though the text of the first and second words is the same, the word location comparison engine 216 may determine that the first and second words are not corresponding to be included in a word pair because of the difference in the size of the words. For this example, FIG. 5 and FIG. 6 show two variants of a layout. Document 602 (FIG. 6) has the same layout as the document 502 (FIG. 5) with different content. The word "INVOICE" appears two times as the word 504, and the word 506, that is below the word 504, in the document 502. The word "Invoice" appears two times as the word 604, and the word 606, that is below the word 604, in the document 602. With the two words 504-506 and 604-606 in the two documents 502 and 602, there can be four combinations or four possible word pairs. A word pair will include one word from each document. A first combination is the word "INVOICE" 504 and the word "INVOICE" 604, a second combination is the word "INVOICE" 504 and the word "INVOICE" 606, a third combination is the word "INVOICE" 506 and the word "INVOICE" 604, and a fourth combination is the word "INVOICE" 506 and the word "INVOICE" 606. Comparing the size or checking the size of words excludes the second and third combinations as possibilities. Such comparisons can also serve to exclude words of different sizes on unrelated documents.

The word location comparison engine 216 may limit the search of other words to a predefined threshold area. A reason for limiting the search of other words to the predefined threshold area is that scans often introduce an offset, as well as rotations and scale. Therefore, words of the same document often will not appear in the same place. It may also help if the bottom-half of an invoice, or other document, "floats." For example, the threshold area may be a circle having a radius of 18 millimeters, which may be 200 pixels at 300 dots per inch (DPI). Using this threshold area helps to improve computational efficiency by reducing the number of word pairs found. However, the word location comparison engine 216 can work with a circle of any radius, including an unlimited or infinite radius. A larger radius can allow for larger transformations, and hence better training or classification. The tradeoff can be computational efficiency because a large radius can be more costly.

Figure 10:
FIG. 10 illustrates a grid being applied to an example document for grouping and creating document classes, under an embodiment.

FIG. 10 and FIG. 11 illustrate a grid being applied to example documents. The word location comparison engine 216 may apply a grid to documents for searching for words for a word pair. The documents 1002 and 1102 have been partitioned, segmented, or divided into a set of tiles. The grids illustrated in FIG. 10 and FIG. 11 are a seven by five gird, with seven rows and five columns, for a total of 35 tiles. However, a grid may have any number of desired rows and any number of desired columns, such as, a five by five grid, an eight by nine grid, a six by eight grid, and so forth.

As illustrated by FIG. 10, tile 1004 has grid coordinates [row 2, column 1]. The tile 1004 includes a word "Peter"1006. The size of the grid may identical to the size of the radius discussed above. In this way, a word that appears two grid spaces away cannot be closer than this radius. Using a grid is an optimization. Generally, it can be desirable to limit the size of the radius in order to make effective use of the grid. The word location comparison engine 216 may access a tile having the same or adjacent grid coordinates in another document to search for a corresponding word in the other document. For example, the word location comparison engine 216 can use grid coordinates [row 2, column 1] to access a tile 1104 in the document 1102 to search for a word for a word pair that corresponds to the word "Peter" 1006, which is in the tile 1004 in the document 1002. Searches for a corresponding word in other documents may be limited to a tile having the same or adjacent grid coordinates. For example, the word location comparison engine 216 may search for a corresponding word on the document 1102, limited to a tile having grid coordinates [row 1, column 1], a tile having grid coordinates [row 1, column 2], a tile having grid coordinates [row 2, column 1], a tile having grid coordinates [row 2, column 2], a tile having grid coordinates [row 3, column 1], a tile having grid coordinates [row 3, column 2], or combinations of these grid coordinates. The word location comparison engine 216 may use such a grid to help reduce processing resources when searches for corresponding words can be limited to specific areas of documents.

In this example, the tile 1104 includes a word "Peter" 1106, a word "Canyon" 1108, and a word "Phone" 1110. A tile 1112 includes a word "Phone" 1114. These words may potentially correspond to the word "Peter" 1006 from the document 1002. The word location comparison engine 216 may identify both the word "Phone" 1110 and the word "Phone" 1114 in the document 1102 as potential matches for a word "Phone" 1008 in the document 1002. This matching can be filtered later during the exact positioning process in the second phase of the processing. The word location comparison engine 216 may calculate a first factor including a Levenshtein distance between the word "Peter" 1006 in the document 1002 and each of the words 1106, 1108, 1110, and 1114 in the document 1102. The word location comparison engine 216 may calculate a second factor that includes a difference between an area size of the word "Peter" 1006 in the document 1002 and area sizes for each of the words 1106, 1108, 1110, and 1114 in the document 1102. The word location comparison engine 216 may select the word "Peter" 1106 from the document 1102 as the word that corresponds to the word "Peter" 1006 in the document 1002 based on the first factor, the second factors, or a score of the factors, Having generated a set or list of word pairs, the word location comparison engine 216 continues on to the next phase of the processing, which is stricter about the position. In this phase, the processing discussed below is repeated for a range of rotations and scale. In some cases, it is sufficient to do a transformation to the bounding boxes of the set of words in one of the documents and pick the transformation with the best score. The word location comparison engine 216 uses the list of pairs of words generated in the first phase as the input for the second phase.

The word location comparison engine 216 first splits the word pairs list into "top" and "bottom" words and independently processes both of these sub-lists. The word location comparison engine 216 divides a document into a top portion of the document and a bottom portion of the document. The word location comparison engine 216 associates a first sub-list of word pairs with the top portion of a document and includes words from the top portion of the document. The word location comparison engine 216 associates a second sub-list of word pairs with the bottom portion of a document and includes words from the bottom portion of the document. The word location comparison engine 216 may divide the document image in half or evenly so that an area of the top portion of a document is equal to an area of the bottom portion of the document. However, the word location comparison engine 216 may split the document into any number of portions as desired, including two or more unequal portions.

One reason for splitting documents is that in invoices and such, there is often a top and bottom that float with respect to each other. In many documents, there are often variable-sized sections in the middle of a document, such as an invoice with a list of items. Therefore, the position of words appearing near the bottom is often not fixed with respect to the words at the top. For example, there may be two invoices that belong in the same class. A middle portion of a first invoice may include a first number of invoice items, while a middle portion of a second invoice may include a second number of invoice items, which are different from the first number of invoice items. The word location comparison engine 216 may split the document into two zones, including a top and bottom zone. These zones are allowed to float with respect to each other. The choice of the middle of the page can be arbitrary and the word location comparison engine 216 can analyze more than one split location.

The word location comparison engine 216 computes first location information for a word of a word pair in act 904. The first location information indicates a location of a word in a first document relative to one or more other words in the first document. The word location comparison engine 216 computes second location information for a corresponding word of the word pair in act 906. The second location information indicates a location of a corresponding word in a second document relative to one or more other words in the second document. The word location comparison engine 216 computes a score based on a comparison of the first and second location information in act 908.

The word location comparison engine 216 finds the words in common by taking each word pair as a "center" and calculating the vectors to one or more other words on both of the document images. If the vector(s) is approximately the same for the two images, then the word location comparison engine 216 adds the word pair to a list. The word location comparison engine 216 may evaluate vectors as approximately equal if the difference vector has a length or absolute value less than 15 pixels at 300 dots per inch, which may be 1.27 millimeters, but this can difference vector can be a tunable or user-configurable parameter.

Figure 12:
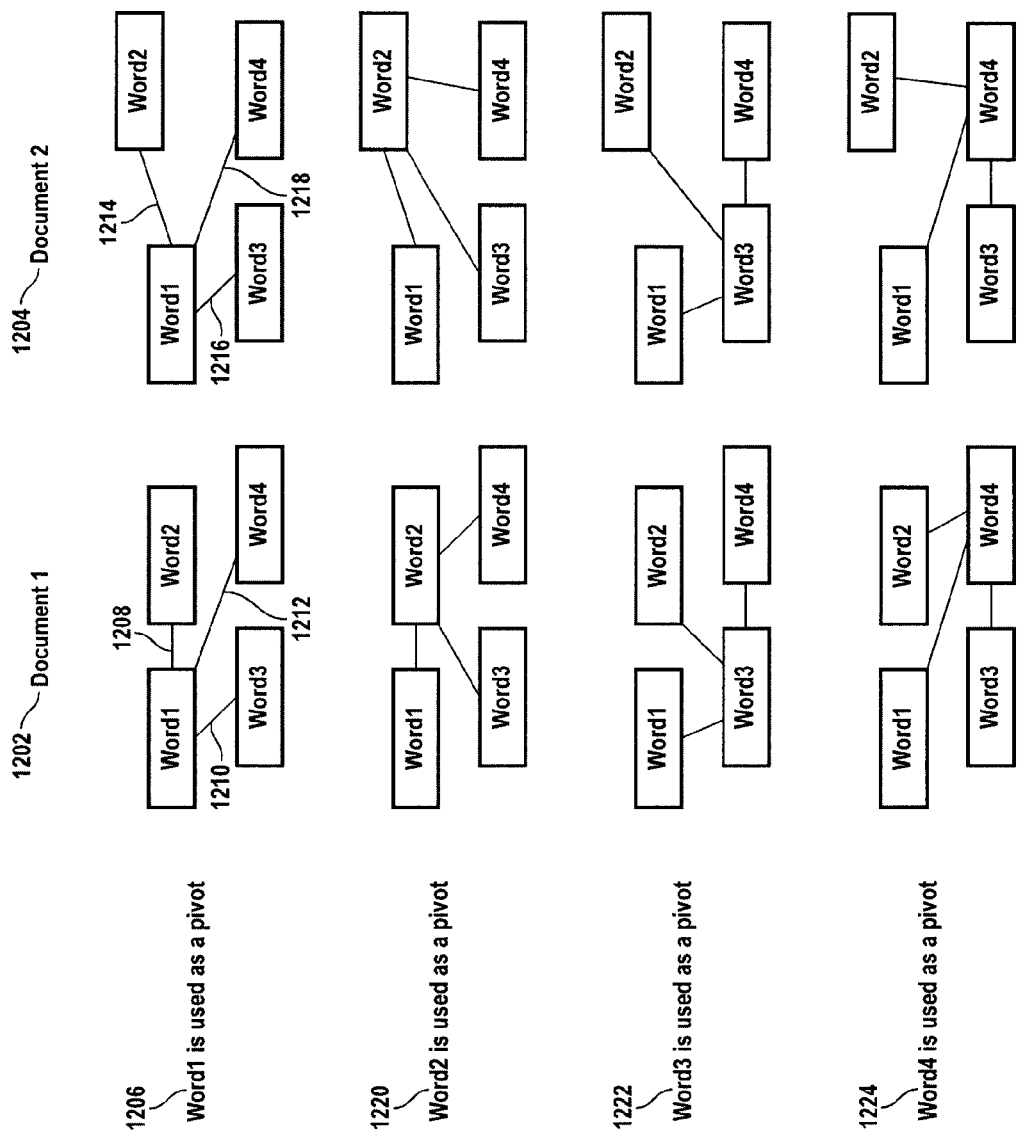
FIG. 12 illustrates a schematic diagram for using spatial relations of words to determine whether two documents should be in the same or different classes, under an embodiment.

FIG. 12 illustrates a schematic diagram for using spatial relations of words to determine whether two documents should be in the same or different classes, under an embodiment. The word location comparison engine 216 may use different words in a document as pivots to calculate a location of a word in a document relative to or with respect to other words in the document. The first document 1202 and the second document 1204 illustrate graphical representations of positions or locations of words. The first document 1202 includes four words: word 1, word 2, word 3, and word 4. The second document 1204 includes four corresponding words: word 1, word 2, word 3, and word 4. In the first document 1202, word 1 is on a same line as word 2 and is to the left of word 2, while word 3 and word 4 are on a line below, with word 3 is offset to the right from word 1, and word 4 offset to the right from word 2. In the second document 1204, word 2 is on a different line from word 1, as word 2 is above and to the right of word 1.

In a first iteration 1206, the word location comparison engine 216 uses word 1 as a pivot, and calculates the vectors in each document image (vector (word 1, word 2), vector (word 1, word 3), and vector (word 1, word 4)). For example, for the first document 1202, a line 1208 represents a first vector calculation from word 1 to word 2, a line 1210 represents a second vector calculation from word 1 to word 3, and a line 1212 represents a third vector calculation from word 1 to word 4. For the second document 1204, a line 1214 represents a first corresponding vector calculation from word 1 to word 2, a line 1216 represents a second corresponding vector calculation from word 1 to word 3, and a line 1218 represents a third corresponding vector calculation from word 1 to word 4.

Generally, a vector is a quantity that has magnitude and direction. A vector may be represented graphically by a directed line segment whose length represents the magnitude and whose orientation in space represents the direction. A vector that indicates a location of a first and second word relative to each other may include a first and second set of coordinates. Each coordinate may include a first component and a second component, or an x-axis component and a y-axis component. A difference between the first components of the first and second set of coordinates may indicate a horizontal distance between the first and second words. A difference between the second components of the first and second set of coordinates may indicate a vertical distance between the first and second words.

In this example, the only combination that is different is vector (word 1, word 2). Therefore, the word location comparison engine 216 creates a list of word 1, word 3, and word 4. For the following iterations, the word location comparison engine 216 makes the same vector calculations for word 2, word 3, and word 4. In a second iteration 1220, the word location comparison engine 216 uses word 2 as a pivot, in a third iteration 1222, the word location comparison engine 216 uses word 3 as a pivot, and in a fourth iteration 1224, the word location comparison engine 216 uses word 4 as a pivot. These iterations 1206, 1220, 1222, and 1224 generate the lists: "word 2;" "word 1, word 3, and word 4;" and "word 1, word 3, and word 4." For each list, the word location comparison engine 216 generates a score and selects the list with the best score. The score is based on the number of common words, their size, or both. The score may instead or additionally be based on other things such as the distribution of the words on a page, such as more spread out words might lead to a better score. The word location comparison engine 216 then combines the lists generated from the top and bottom zones and calculates the score for the combined lists. The word location comparison engine 216 compares the score to a threshold value or threshold score. Based on the score, the classification module 218 determines whether or not the first and second documents are determined to be in the same or different class.

The scoring function takes the list of pairs of words in common between the two images. The scoring function takes the form of Score=$\alpha$CharacterCount+$\beta$CharacterArea, where $\alpha$ and $\beta$ are selected as appropriate for the particular application. The variable or parameter $\alpha$ may be referred to as WeightCharacter, while the variable or parameter $\beta$ may be referred to as WeightArea. The variable CharacterCount may be the sum of the number of characters in the word list. For example, the word "xyz" would count for 3 characters for each pair of words for a total of 6. Fuzzy matching, as discussed above, allows the word pairs to have different character counts. The variable CharacterArea is the sum of the area of each character in both words in the pair. Using character count instead of a word count weighs larger words more than smaller words. The same principle applies to the area. Larger words are emphasized over smaller words because large words are often important distinguishing features, such as headers or logos. The value of $\alpha$ may be 0.4 and the value of $\beta$ may be 0.000875. These values were arrived at after extensive experimentation, and were found to provide good results based on the particular documents that the classification module 218 was designed to group and classify. It should be appreciated, however, that these values may vary greatly in other applications or configurations of the system. For example, the values of $\alpha$ and $\beta$ may vary depending on the particular document types to be grouped and classified, such as invoices versus benefit claims. The area may in 300 dots per inch pixels. Appropriate scaling would be done if the resolution were different.

If the calculated score is larger or greater than a desired threshold, which is not independent of $\alpha$ and $\beta$, the classification module 218 may evaluate the document images as in the same class. If the calculated score is less than the desired threshold, the classification module 218 may evaluate the document images as not in the same class. The threshold may be 210, but the threshold value can vary greatly depending on factors such as the particular document types to be grouped, and others.

Using the specified values above for $\alpha$, $\beta$, and the threshold, the equation to determine whether documents are in the same class may be the following: 0.4 CharacterCount+ 0.000875 CharacterArea>210. This may be approximately equivalent to about 30-40 words, depending upon the size of words.

The word location comparison engine 216 might not normalize the score by the number of words that appear on the document. Other approaches include normalizing the score based on the number of words on each image. The idea is that the number of common words that indicate that two images are the same will be roughly constant across different invoice and form types. However, if the word location comparison engine 216 normalizes the score based on the number of words in the image, the word location comparison engine 216 will penalize documents that have many non-common words, such as documents with 90% of the words that are not in common. For example, the example invoices illustrated by FIG. 3 and FIG. 4 are in the same class, and each invoice includes many listings of items that are different from the listings of items on the other invoice. Normalizing the score by the number of words may then result in the classification module 218 placing the two invoices in different classes because of the differences found in the listings of invoice items. The scoring function may be non-linear, there may be non-linear terms in the score, and a score may further be based on the number of words on each page or in each document. For example, the location of the word "INVOICE" 306 relative to the word "DATE" 308 in the document 302 is similar to or approximately the same as the location of the word "INVOICE" 406 relative to the word "DATE" 408 in the document 402, thereby adding to the evidence that documents 302 and 402 should be in the same class.

Figure 13:
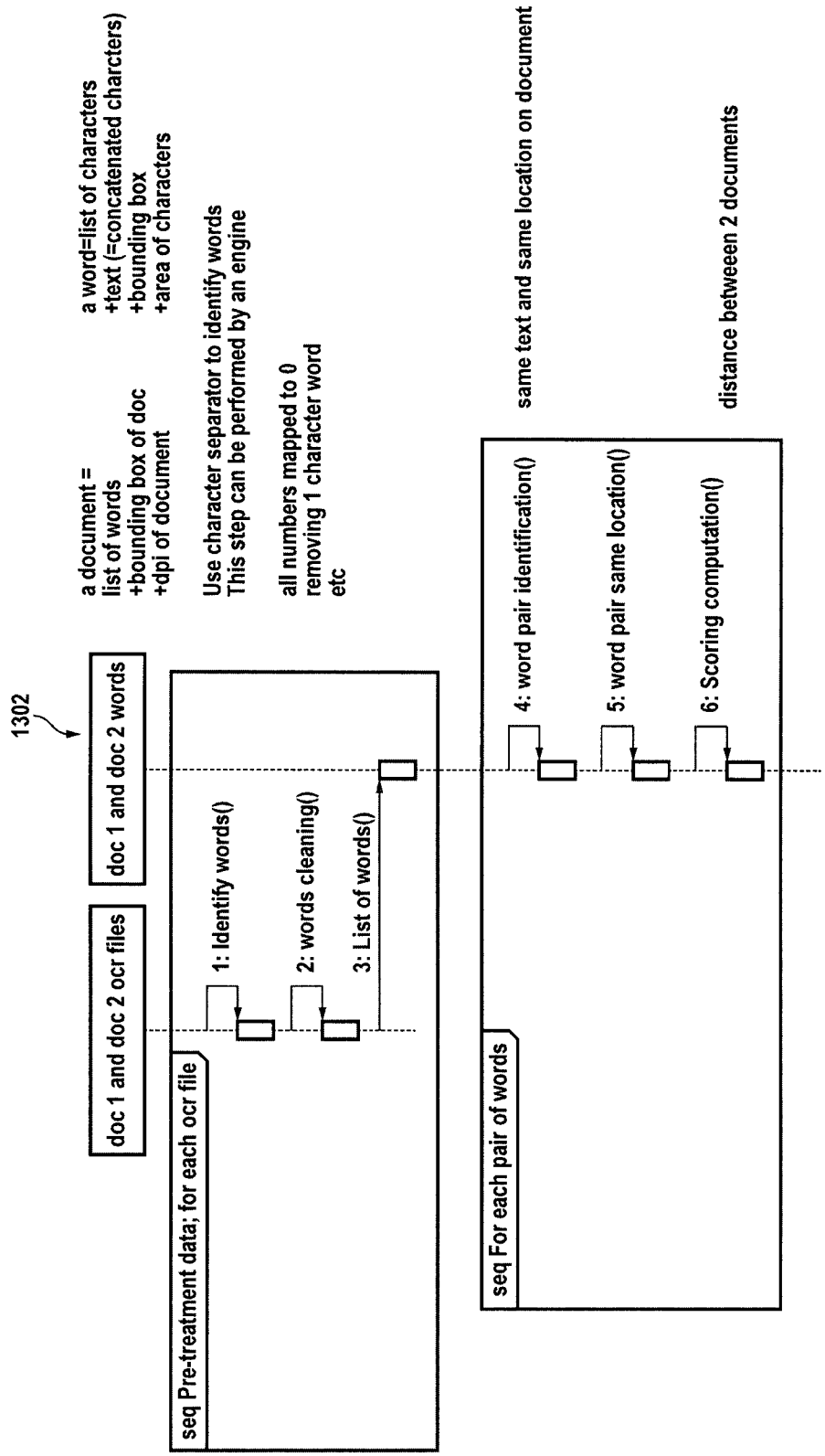
FIG. 13 illustrates a sequence diagram of a specific implementation of a textual distance function for using optical character recognition data for grouping and classifying documents, under an embodiment.
Figure 14:
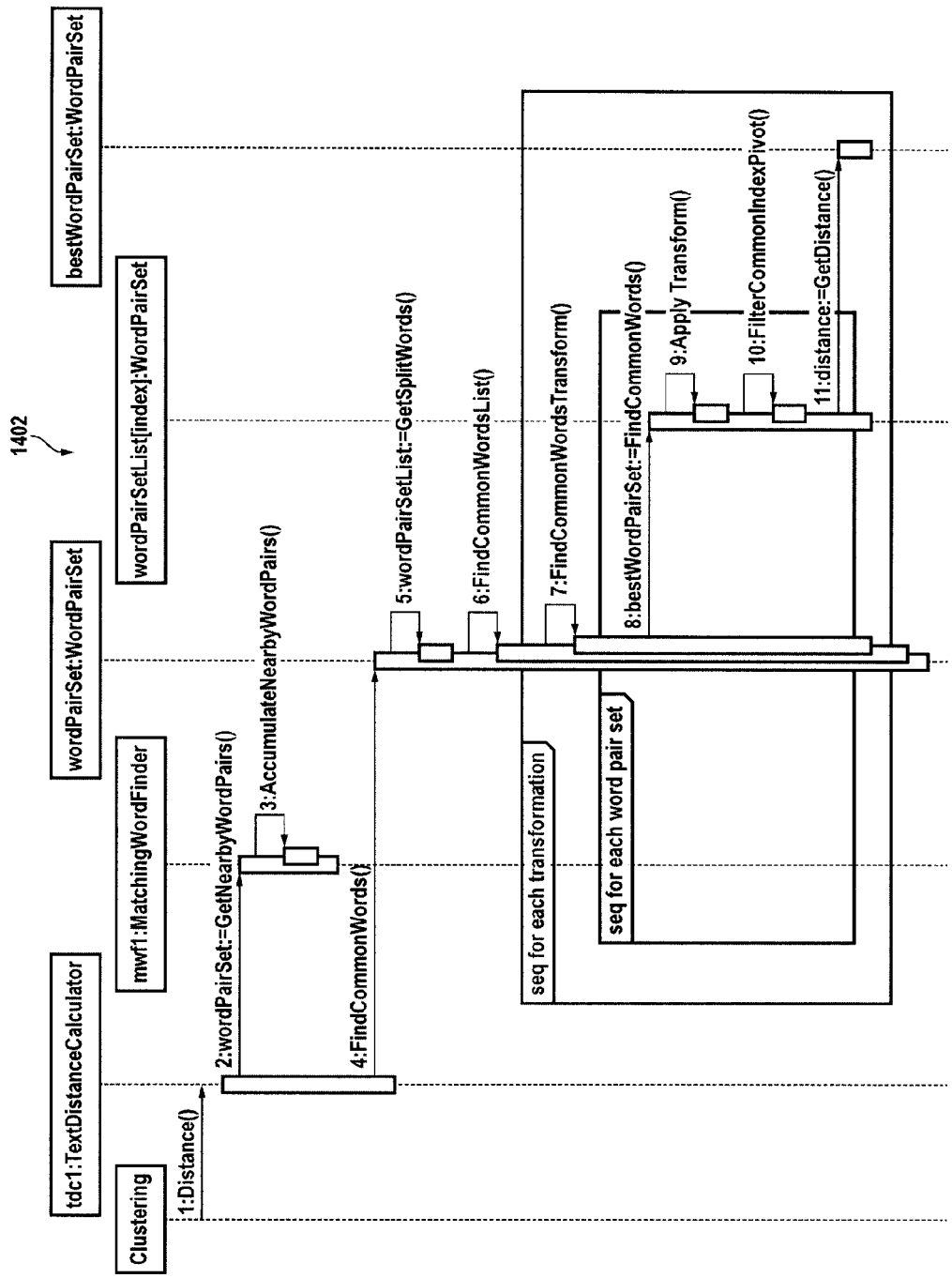
FIG. 14 illustrates a swimlane diagram for the sub-processes of a distance function, under an embodiment.

FIG. 13 illustrates a sequence diagram 1302 of a specific implementation of a textual distance function for using optical character recognition data for grouping and classifying documents, under an embodiment. FIG. 14 illustrates a swim-lane diagram 1402 for the sub-processes of a textual distance function, under an embodiment. The diagrams 1302 and 1402, and the accompanying discussion, are merely examples of using the spatial relations of words to group and classify documents. Other similar and equivalent elements, functions, object classes, and components may be used or substituted in place of what is shown.

The diagrams 1302 and 1402 and the accompanying discussion describe an example of a textual distance function that can compare documents based on textual data, such as optical character recognition data, in order to determine whether two or more documents are similar or not. In this example, the textual distance function includes two variants: a clustering version and a classification version. These variants differ in the manner in which the score is generated, but are generally equivalent. In the case of the clustering version, the document manager application 214 does not know a priori which words should be considered significant, which words should be considered keywords. In the case of the classification version, the document manager application 214 has a reference, a list of keywords, in which words in that reference are considered significant.

The inputs include documents, and each document includes a list of words and bounding box of the document. A word includes a list of characters, text (concatenated characters), a bounding box, and an area of characters. The area is the sum of the width multiplied by the height of each individual character, which may be different when there are rotated words, rather than the width multiplied by the height of the word's bounding box. However, the area may be the width multiplied by the height of the word's bounding box. The coordinates may be in a dots-per-inch-independent coordinate system. A document may include other information, such as the location of graphical zones. The textual distance function may take into account the placement, content, or both of graphical zones.

The output of the textual distance function includes a distance value or score that may range from about 0 to 255, where a score of 0 indicates that the two documents are very close or similar, and a score of 255 indicates that the two documents are not similar at all. However, the range may be scaled differently as appropriate for a particular application and environment. In this example, there is a class referred to as TextData which represents the document, and a class referred to as TextWord which represents a word.

The diagram 1302 illustrates a flow for using spatial relations of words to group and classify documents. In step 1, optical character recognition data is read. The output from a scanner may include an optical character recognition file that includes a list of characters. The words may not be separated, but the list of characters may include separator characters, such as blanks, \t, or \n. The textual distance function parses the optical character recognition file to divide the list of characters into words. The textual distance function's code component that reads the optical character recognition file is responsible for creating a TextData class. In step 2, data is pretreated. The textual distance function transforms the optical character recognition data into data that facilitates computing the spatial relationships among words and provides good performance. The class TextualDistanceCalculator performs this transformation in its constructor and implements the distance function by comparing against another TextualDistanceCalculator object rather than directly comparing with TextData. In step 3, a distance algorithm is applied. The distance algorithm takes two documents and finds the list of word pairs, one word from each document, which obeys a set of constraints and maximizes a scoring function.

As part of the pretreatment step, the textual distance function removes a predefined set of words, including words that have a single character, and alters the text where the differences are not considered by the algorithm. This altering of the text is a performance enhancement, and it could be just as easily done later during the comparing of text. As discussed above, the pretreatment step may include mapping all numbers to a predefined value, such as "0," and rejecting words with only a single character, which are often noise or the interpretation of a graphic as a letter. Other filters may be used instead or additionally. For example, a period ('.') and a comma (',') might be confused often enough by the optical character recognition engine such that the textual distance function may treat such characters as the same. Other pre-filtering techniques to help compensate for characters that may confused by the optical character recognition engine include mapping upper case letter "I," the lower case letter "L," and the number "1," to the same predefined character, and mapping the number "0" and the upper case letter "O" to the same predefined character. It is desirable to keep track that the word has changed. The fact that a word has been modified is used to lower the weight of a word during a keyword learning step, and it can also be useful to use this in the distance function itself.

As discussed above, one reason for mapping all numbers to a predefined value, such as "0" is that variable number fields may be in the same place but with different numerical values. Therefore, the word location comparison engine 216 treats "123.45" and "567.89" as equivalent. The Levenhstein distance helps to make comparisons with variable number of digits. The application of the Levenhstein distance may result in a first word including a first number of digits being matched to a corresponding second word including a second number of digits, different from the first number of digits. For example, the text "1234.56" may be made equivalent to "987.65." The confidence values of characters, their alternates, or both, may instead or additionally be used to match or identify a word and a corresponding word.

The pretreatment step, as described below, may include creating a 2-dimensional array of lists of words, stored in the MatchingWordFinder class. As discussed, the distance algorithm can take two documents and find the list of word pairs, one word from each document, which obeys a set of constraints and maximizes a scoring function. The constraints on this list of word pairs may include a first constraint that a word must be the "same" or equivalent on both document images. A second constraint may specify that the set of words from a first image must be close to the same relative position on a second image. Relative position provides that after a transformation is applied to the coordinates of the set of words on an image (the transformation allows for translation, scaling and rotation) that the boxes are in the same position (such as less than 15 pixels at 300 dots per inch) in the two documents. The algorithm divides the words into top and bottom zones with independent translations, but not independent scale and rotation. The transformation is the same for each word. The range of transformations to test for is a set of parameters that can be tuned, configured, or adjusted as desired. Generally, the larger the range, the longer the algorithm takes, but the more accurate the algorithm will be.

Words may be the "same" or equivalent on two images if the distance between the centers of each word is less than or below a threshold value, such as 200 pixels at 300 dots per inch. This threshold parameter helps to limit the number of choices considered in order to conserve computing resources and help ensure rapid code execution. However, the threshold parameter may be set to infinite in certain applications. Words may be the "same" or equivalent on two images if the area is about the same, such as if a difference between the areas must be less than 50 percent. That is, a parameter AreaTolerance=0.5 so that the areas for two words to be equivalent cannot be more than 50 percent different. However, the parameter can be configurable and can be set to any threshold value. Words may be the "same" or equivalent on two images if the text is about the same based on a value of a string metric, such as the Levenhstein distance is less than a LevensteinThreshold.

The scoring function for the clustering distance may be: Score=Sum for all matching words (WordArea*WeightArea+NumberCharacters*WeightCharacter). As discussed above, WeightArea and WeightCharacter may be represented by the variables or parameters $\beta$ and $\alpha$, respectively. From this the system obtains a "distance" by calculating: Distance=TextDistanceParameters.BaseScore−Score. If the result of the distance calculation is less than 0, the distance may be set to 0. Likewise, if the result of the distance calculation is greater than 255, the distance may be set to 255. Through experimentation, this scoring was determined to provide good results. The distance function may look for an absolute number of words in common, and not a relative number of words in common. However, the distance function may instead or additionally look for a relative number of words in common.

As discussed, the use of the area in the score provides that words in a larger font size are weighted more than those in a smaller size. One reason is because that for certain document types large words tend to be things such as logos that are likely more significant than smaller words. This is not, however, necessarily always the case. For example, depending upon the document types to be classified, words in a larger font may not be weighted more than words in a smaller size. For example, words in a larger font may be weighted the same as words in the smaller size, or words in a larger font may be weighted less than words in the smaller size.

The textual distance function may include a normalization technique to help ensure that the distance between two blank documents is the same. The normalization technique, however, is not a strict percentage, such as a distance of 128 for 50 percent of words in common. One advantage of not normalizing using a strict percentage is because on some documents of interest, there may be a lot of words that can be irrelevant, such as rows in an invoice. It may be desirable to be insensitive to this sort of variation. For example, finding 50 words in common may indicate the same document type. If the word location comparison engine 216 finds 50 of 150 words in common between two documents, the distance between these documents may be close to 0. However, if the word location comparison engine 216 finds 1 of 3 words in common between two documents, this finding may not be very significant.

Figure 15:
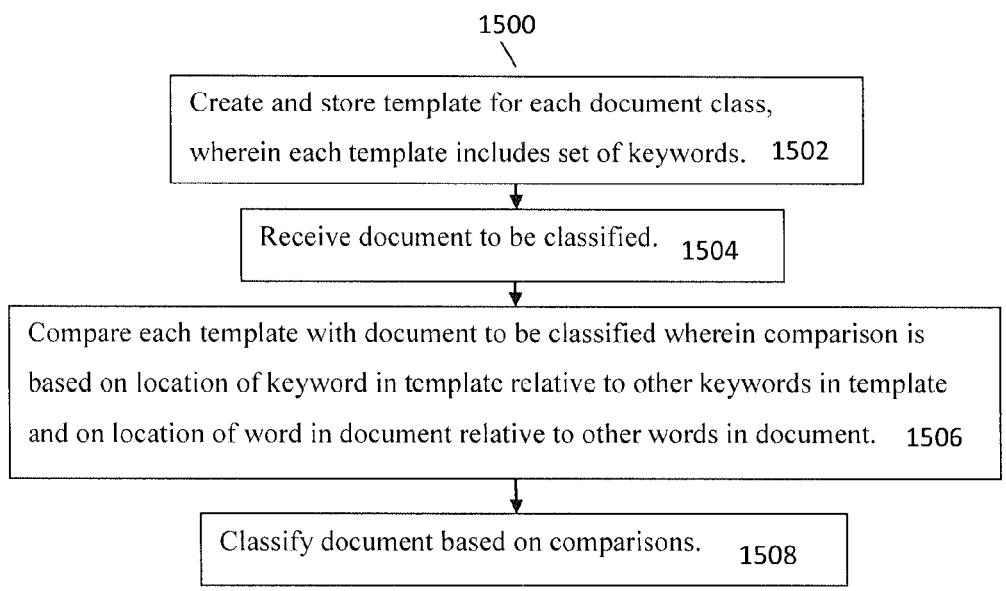
FIG. 15 illustrates a flowchart for creating document templates and classifying a document using the document templates, under an embodiment.

The word location comparison engine 216 may be further adapted for scoring for classification distance, with the list of template keywords being the same structure as the list of words. One difference, however, may be the scoring function. The scoring function may be different because the document manager application 214 knows that the list of keywords should be present. As discussed, when comparing two unknown images the document manager application 214 may not have information about which words should be present, but when the document manager application 214 has the keywords a word being absent may be significant. The description below of FIG. 15 provides a more detailed discussion of document templates.

The word location comparison engine 216 may be implemented using two main phases. In a first phase, the algorithm finds a list of nearby word pairs that are the same or equivalent words in two documents. In a second phase, the word location comparison engine 216 refines the list to find the list of words that are in about the same position, after a transformation, in the two documents.

For finding nearby words, the first part of the word location comparison engine 216 is implemented in MatchingWordFinder. The constructor of MatchingWordFinder takes a list of words and breaks them up into a grid of lists of words organized by the position of each word. Each element of the grid represents an area on the image of RectDistThreshold× RectDistThreshold. For example, position [3, 5] has a list of words whose centers are between 3*RectDistThreshold<=x< (3+1)*RectDistThreshold and 5*RectDistThreshold<=y< (5+1)*RectDistThreshold. This grid is created once per document and is reused for each call to the distance function.

The routine GetNearbyWordPairs takes two MatchingWordFinders and creates a list of WordPairs (WordPairSet) for the words that are the same in each document. Because the document manager application 214 looks for words whose centers have a distance<RectDistThreshold, the search can be limited to the neighboring grid areas. Below is a code sample:

```
WordPairSet wps=new WordPairSet( )
  For each Image1.GridElement
    For each Image2.GridElement that is within 1 element
      (x±1, y±1) of Image1.GridElement
      AccumulateNearbyWordPairs(wps,
Image1.GridElement.WordList,
Image2.GridElement.WordList)
```

The AccumulateNearbyWordPairs iterates though every combination in the two lists, and a word might appear multiple times in each list. For example, the word "x" might occur on a second image in several places. In this case, the word location comparison engine 216 adds one pair for each occurrence. Duplicates are filtered out in the second phase of the process because at this point the word location comparison engine 216 does not know which "x" is going to be in the same relative position.

With the set of nearby word pairs, the word location comparison engine 216 moves to the second phase for finding words in the same relative position. The word location comparison engine 216 looks for the list of words that maximize a scoring function that are on the two images and are in the same place on both images. Specifically, the image is divided into "top" and "bottom" words. As discussed above, on some documents such as invoices, the top and bottom portions vary with respect to each other. On forms or other document types, splitting the image has been found unlikely to cause a loss of accuracy.

Then, the word location comparison engine 216 finds the set of words in the same place after a transformation is applied using variations of scale and rotation. The transformation helps to ensure that word coordinates or locations can be compared.

For each Transformation t
  FindCommonWords(t)

The document manager application 214 takes each word in the word set and uses this as a pivot to find the common words. With this pivot word to find the common words, the word location comparison engine 216 takes each other pair of words and calculates the vectors:
img1.wpivot.bounds.Center-img1.w.bounds.Center and
img2.wpivot.transformedBounds.Center-
img2.w.transformedBounds.Center If these vectors are close, such as the difference between these vectors has a length less than 15 pixels at 300 dots per inch, then the word location comparison engine 216 determines that the associated words are in the same position and adds these words to the list. An optimization technique may apply the vector calculation to at most a subset of words because applying the vector calculation to every third word can improve performance without degrading the results. The word location comparison engine 216 applies the vector calculation for both the "top" and "bottom" lists and makes one list of top+bottom. A vector calculation is made for each pivot, and for each list a score is calculated. The word location comparison engine 216 identifies the "best" list, such as the list that maximizes the score. In the function, this list may be returned so that this list can be used in the word location comparison engine 216 for learning keywords.

FIG. 15 illustrates a flowchart for creating document templates and classifying a document using the document templates, under an embodiment. The document manager application 214 creates and stores a template for each document class, act 1502. Each template includes a set or list of keywords. The templates may be stored in a template database. The document manager application 214 receives as input a document to be classified, act 1504. For example, the document may be received from a scanner or other optical character recognition data-stream. The document manager application 214 compares each template with the document to be classified, act 1506. Each template in the set of templates may be tried. The comparison is based on the spatial relations of the keywords in a template and the words in the document to be classified. More particularly, the comparison is based on a location of a keyword in a template relative to other keywords in the template, and on a location of a word in the document relative to other words in the document. The document manager application 214 classifies the document in response to the comparison, act 1508.

In a specific implementation, a document template associated with a document class includes a set of keywords and location information indicating a location of a keyword in the template relative to one or more other keywords in the template. Upon creating the set of document classes based on grouping the set of training documents, the document manager application 214 can create a document template to be associated with each of the document classes. In other words, once there is a set of document images that are of the same class, the document manager application 214 determines a set of words that appear in all (or at least most) of the documents. The set of words may be referred to as the keywords of a template. It is also possible for a user to define this list of keywords. The list of keywords may include words provided by the document manager application 214 based on analysis of the documents, words provided by a user, or both.

A keyword learning algorithm may take the collection of document images in a class and output a set of words in common. The algorithm starts by getting or obtaining the common set of words between each pair of documents. This can be accomplished using the same algorithms in the distance function discussed above.

The document manager application 214 then creates a matrix of words in each document (e.g., docCount X words). For each pair of words in the common words set of each pair of documents, the document manager application 214 executes the following procedure (for documents i, j):
1. If the word x already exists in the list either document add in the new pair (note that one of these words must already be there)
  a. If (not null words[x][i])
  words[x][i]=wordPair.word(doci)
  b. If (not null words[x][j])
  words[x][j]=wordPair.word(docj)
2. If it does not exist, then add the pair to the list
  a. words[x][i]=wordPair.word(doci)
  b. words[x][j]=wordPair.word(docj)

This generates a list giving the information, for example, "the word X appears in the documents A, B, C and D," "the word Y appears in the documents A and D," and so forth. The list may include a word, and a number of documents that the word has been found in, an identification of the documents that the word has been found in, or both. The document manager application 214 may sort this list by another scoring function, which is a different scoring function from the distance function, which takes into account the number of documents a word is found in, the size of the word, and whether or not it is an exact match.

The document manager application 214 selects the top N words that have a score at least equal to a threshold. The value of N may range from about 30-40. Generally, more words may provide more accurate results, but may increase the processing time when using the words in classification. Therefore, depending on the specific application of the document manager application 214, the desired accuracy, and available computing resources, the value of N may be less than 30 or greater than 40. The document manager application 214 then transforms its box into a common coordinate system for each word. The first document image in the set may be identified as the "master" document image providing the coordinate system. This choice is arbitrary. The bounding box for a word may be: Average(Transform(master, i) (word.Bounds(doc i)). The word text to be used is the word which occurs most often or most frequently. As discussed, the text might be slightly different in each word because of the fuzzy word match. The output includes a set of words, such as keywords that are common across a set of document images in a class.

The document manager application 214 may create a document template that includes the keywords. Upon receipt of a document to be classified, the document manager application 214 compares the document against the template and classifies the document based on the comparison. The template may include a set of keywords and first location information that indicates a location of a keyword in a template relative to one or more other keywords in the template. The document manager application 214 receives a document to be classified. The document manager application 214 selects a template, which may be based on a scoring function for classification between a document image and a set of keywords. Generally, the classification scoring function includes more or additional information than the training scoring function. As discussed above, one reason is because through the keyword learning algorithm, there is a list of words, such as keywords, that ought to be on a given document image if it is in the given class. This is in contrast to the training function which is looking for similarities between two document images with no a priori knowledge of the contents of the two images. This difference can change the underlying form of the function.

However, due to training errors, optical character recognition errors, and other problems with the document image, there may not be 100 percent of the keywords of a template found in the received document. For example, the document manager application 214 may find that an address that is the same for all the training samples but is actually changed in a real situation.

The scoring function can use the same word-finding algorithm as in the training distance function. A score is calculated that indicates the percentage of words found. If there are a sufficient number of words found, the document should be able to be classified. The percentage of words found can be compared to a threshold value, such as a threshold value of about 65 percent, but the threshold value can vary depending upon the application and desired results. The code sample illustrates some possibilities:

```
const int maxWords=30; \\ this can be changed
commonWords=GetCommonWords(keywords, image);
countDoc min(keywords.Count, maxWords);
countRef min(commonWords.Count, maxWords);
score=commonWords.Count/keywords.Count;
boolean isClassified=(score>threshold);
```

To classify a document using a template, the document manager application 214 generates a set of word pairs. Each word pair includes a keyword from the set of keywords of the selected template and a corresponding word from the document to be classified. The document manager application 214 computes second location information for a corresponding word of a word pair. The computed second location information indicates a location of the corresponding word of the word pair in the document to be classified relative to one or more other words in the document. The document manager application 214 compares the second location information against the first location information and returns a score responsive to the comparison that can be used to determine whether or not the received document should be classified in the document class associated with the template. Classifying the document in the document class may include tagging the document with a tag or other metadata information that indicates the document class.

In addition to the spatial relationships of words, the document manager application 214 may also extend the search for common words to graphics including pictures, photographs, graphical images, graphical symbols, and charts, such as pie charts, bar charts, or graphs. A technique for grouping and classifying documents with graphics may include finding zones of graphics and a function to determine whether graphics are the same or equivalent. If the same graphic appears in the same position, it adds to a confidence rating indicating that it is the same document. This can be mixed with the textual matching.

The document manager application 214 may be adapted to words, such as a group of two or more characters, rather than individual characters, or the document manager application 214 may be adapted for individual characters, groups of words, such as sentences, phrases, paragraphs, a document line, or combinations of these. When the document manager application 214 is comparing to see if two words are the "same" or equivalent, the document manager application 214 may or may not use character confidences or alternate choices, such as number "0" versus capital letter "O," which may be provided by the optical character recognition engines. Using confidences can enhance the comparisons function. Further, instead of a Boolean decision on sameness or equivalency, there can be a confidence value used in the scoring function.

There can be other separate uses for the underlying textual/position matching algorithm. For example, the document manager application 214 may generate an anchor which includes a collection of words around a field, such as the words "total," "tax," and "subtotal" which may appear in the same positions consistently, such that if two of the three are found one may be fairly sure to have found the right place. Using a collection of words as an anchor offers benefits over using a single unique text or graphic to locate a field because there can be problems with noise or markings, such as handwriting, on a document image.

Using the spatial relations of words to determine whether two documents belong in the same document class has advantages over graphical-based distance functions for training and classification. Typically, graphical-based distance functions "blur" an image or use low-resolution reductions in order to ignore variations such as different words, and so forth. This technique may be adequate for document images that do not change much from one document to another of the same class, such as in forms where the majority of the image comes from the underlying form or where the graphics are particularly bold, such as invoices that have a lot of black pixels in the underling template. However, when the document images have fewer graphics and the pages are generally lighter, small variations such as stamps tend to greatly skew the distance function. For example, documents 302 and 402 may be placed into different classes by such a distance function even though to a human eye they may be related. The stamp 312 and the noise in the document 302 may cause this graphical distance to become large. Further, the differences in the content of invoices, with varying number of lines, invoice items, or both, can confuse other classification algorithms. In the case of semi-structured documents such as invoices, graphical differences within the same type of documents can be large, especially when an invoice has a variable sized table. This may result in substantially sub-optimum grouping and low classification rates.

The distance function, as implemented by the document manager application 214, overcomes these deficiencies and can classify the documents correctly. Further, the document manager application 214 can take into account minor transformations such as small rotations and scaling. For example, scanned images are often rotated because the physical page perhaps was not perfectly placed or aligned on the scantier and notions such as dots per inch may only be approximate and not perfectly consistent from scanner to scanner. The document manager application 214 may be completely scale and rotation independent. The document manager application 214 allows for much higher classification rates and lowers document management and processing costs.

A technique for classifying documents may be based on position and text. A "template" includes N boxes with text, character or word. A character may provide good results, but may increase the processing time. There can be graphic boxes as well. To classify a target document, an optical character recognition is performed on the target to match the N boxes. The template can be shifted around until a desirable match is achieved. This can be accomplished by using boxes+text. OCRd text that is not part of the classification may be ignored.

The document manager application 214 may take a set of images for clustering. The document manager application 214 checks each image one at a time against all the previous images. If a match is found, the document images are placed in the same bucket. An iterative process using progressively higher thresholds for matching may be used for refining. The document manager application 214 may count the number of matched characters and ignore mismatched characters, assuming any mismatch may be due to variable text. To be matching, the same, or equivalent, the relative offsets and sizes of text boxes should be the same or equivalent. That is, if there is a word "X" that is (x, y) away from a word "Y," to match another image the same pair of letters must be the same relative position and the letters must be of the same size. There can be a small margin for variations, such as at most about a tenth of a character in size.

Once a collection of images have been obtained that seem to be of the same collection, using "loose" criteria, the document manager application 214 obtains the set of text/boxes that are common to all, or at least most. Some recognition errors may be tolerated, but the document manager application 214 can be fairly strict, especially when creating the classes, as it is not necessary to have the complete set of words in common.

The document manager application 214 may be biased to weigh larger text more heavily because larger text can be typical of logos. A rotational invariance may be obtained by using distances rather than looking just at delta-x, delta-y. A requirement may be that at least 3 "keywords" are obtained. An optical character recognition engine may provide a larger bounding box for a rotated character which the document manager application 214 can account for. At the end of the classification, there is a collection of templates. Each template includes a set of N keywords including of text positions and values, such as word "x" at (123, 456) of size (20, 20).

At classification-time, the document manager application 214 determines how many of these match and takes the largest number of matches, or highest percentage. The classification algorithm may be similar to the algorithm that makes the clusters. There may be an additional variable for number of lines. A single degree of freedom may be assumed. Some "keywords" could float by the number of lines in the optical character recognition results.

A location or spatial location of a word in a document may be with respect to the centers of other words in a document. That is, a center of a word may be used as a reference point. However, a reference point may not be at the center of a word. For example, the reference point may be at the beginning of the word, the end of the word, or at any arbitrary location within a document, such as the upper left hand corner, the upper right hand corner, the lower left hand corner, or the lower right hand corner.

FIG. 16 illustrates an example of two documents that were grouped together. The documents 1602 and 1604 contain a substantial number of similarities in the header and hence are clearly related. However, the field "amount due" 1604 and the field "amount due" 1606 are in completely different positions in the documents 1602 and 1604, respectively. Therefore, the document manager application 214 creates subgroups for the documents 1602 and 1604 to separately treat these two documents 1602 and 1604.

FIG. 17 illustrates an example matrix for a set of documents that have common words, under an embodiment. The common word matrix may be generated via the common word matrix algorithm described above. In order to subgroup, the document manager application 214 identifies the collection of words in common across the set of documents. In a very simple example, the document management application 214 creates a matrix 1702 with columns for 5 documents and rows for 9 keywords for a class of invoice documents. The "X" represents the presence of the word in a document and, for display purposes, these words are sorted these by the number of times that they appear in the documents. In this example, the "X" in the combination of the first column for Document 1 and the first row for word 1 indicates that document 1 includes word 1. Since the document manager application 214 is evaluating documents that have already been determined to be closely related, some of the words may appear in all the documents, but this is not strictly necessary. The matrix 1702 indicates the presence of two main sub-clusters: documents 1, 3 and 5 appear to include one set of words, while and documents 2 and 4 appear to include a different set of words. In real examples with more words, this sub-clustering may be easy to visually identify.

FIG. 18 illustrates a distance table for a set of documents that have common words, under an embodiment. The document management application 214 identifies a "distance" between each of the pairs of words. This distance is the number of documents that are different in including a corresponding pair of words. The following examples are simplified to illustrate the functioning of the document management application 214, but in the real-world the document management application 214 will be typically dealing with many more words, possibly more than 100 words, and often a greater number of documents. In a very simple example, the document management application 214 identifies the distance between word 2 and word 3 as 1 because the matrix 1702 indicates that all of the 5 documents include word 2 while 4 of the 5 documents include word 3. Therefore, the distance table 1802 indicates this distance of 1 in the intersection of the row for word 2 and the column for word 3 and also in the intersection of the column for word 2 and the row for word 3. In another example, the matrix 1702 indicates that the distance between word 1 and word 2 is 0 because all 5 documents either include both word 1 and word 2 or do not include both word 1 and word 2. This distance of 0 is recorded in the corresponding word 1-word 2 intersections in the distance table 1802. In yet another example, the matrix 1702 indicates that the distance between word 4 and word 6 is 5 because the 3 documents that include word 4 do not include word 6, while the 2 documents that include word 6 do not include word 4. This distance of 5 is recorded in the corresponding word 4-word 6 intersections in the distance table 1802.

The document management application 214 uses the clustering algorithm to create word clusters based on these distances. Not all clustering algorithms will yield the same result, because of the ambiguity about which group some words ought to be in when a clustering algorithm identifies "ties." Each word cluster includes pairs of words associated with a corresponding distance less than a distance threshold. For example, The document management application 214 creates the following word clusters using a distance threshold of 2:

word cluster1: word1, word2, word3;
word cluster2: word4, word5, word9;
word cluster3: word6, word7; and
word cluster4: word8.

In this example, the document management application 214 creates word cluster 2 to include word 4, word 5, and word 9 because the distances between each of the words in word cluster 1 are less than a distance threshold of 2.

Using these clusters, the document management application 214 determines if there are any subgroups that are important by creating a set of these word clusters. The document management application 214 starts with a word cluster and identifies the word clusters that are "complementary" to the word cluster, that is, word clusters that are not associated with any of the same documents as the word cluster. In a very simple example, the document management application 214 identifies a cluster set 1 that includes only cluster 1, a cluster set 2 that includes both cluster 2 and cluster 3, and a cluster set 3 that includes only cluster 4.

cluster set 1: {cluster1}
cluster set 2: {cluster2, cluster3}
cluster set 3: {cluster4}

In this example, the document management application 214 creates cluster set 2 to include word cluster 2 and word cluster 3 because documents 1, 3, and 5 that are associated with cluster 2 are not included in the documents 2 and 4 that are associated with cluster 3. The document management application 214 creates all possible sets of complementary clusters.

Using these sets of clusters, the document management application 214 applies a scoring algorithm, such as the highest total number of words. In other examples, the document management application 214 may apply a scoring algorithm based on the average size of a cluster within a set. The document management application 214 may use other scoring algorithms. For example, the document management application 214 may count the number of words in each set of clusters. In this example, the cluster set 1 includes only word cluster 1, which has 3 words. Further to this example, the cluster set 2 includes word cluster 2, which has 3 words, and word cluster 3, which has 2 words, for a total of 5 words. Completing this example, the cluster set 3 includes only word cluster 4, which has 1 word.

The document management application 214 creates subgroups of the documents. In a very simple example, the document management application 214 divides the documents into 2 subgroups, subgroup 1 for documents 1, 3, and 5, and subgroup 2 for documents 2 and 4, because cluster set 2 includes 5 words, which is more than the number of words included in cluster set 1 or cluster set 3. As a result, the document management application 214 may group documents 1, 3, and 5 together as first pages of invoices and group documents 2 and 4 together as last pages of multi-paged invoices. The document management application 214 starts with a group of related documents and identifies subgroups within the group of documents that are more efficient for processing purposes.

Figure 19:
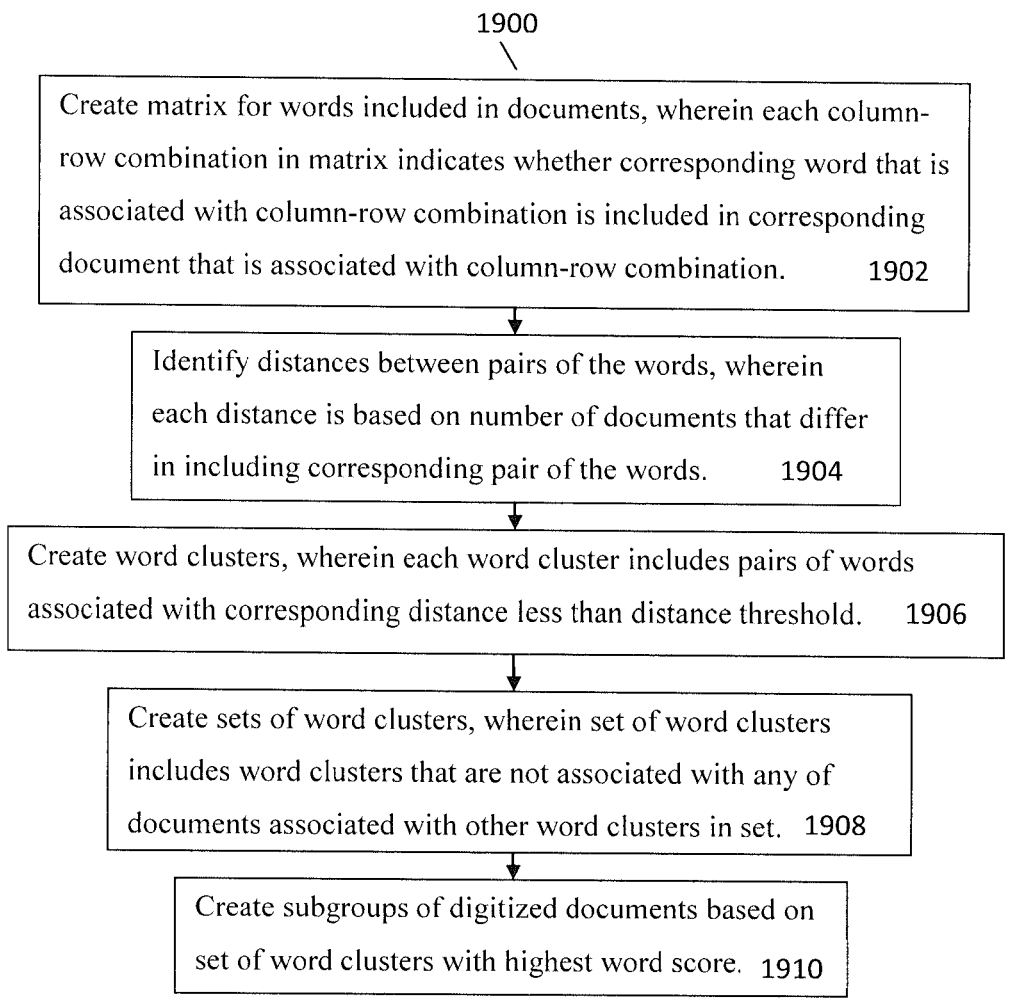
FIG. 19 is a flowchart that illustrates a method for creating subgroups of documents using optical character recognition data, under an embodiment.

FIG. 19 is a flowchart that illustrates a method of creating subgroups of documents using optical character recognition data. Flowchart 1900 illustrates method acts illustrated as flowchart blocks for certain steps involved in and/or between the client 202-204 and/or the servers 206-208 of FIG. 2.

A matrix is created for words included in documents, wherein each column-row combination in the matrix indicates whether a corresponding word that is associated with the column-row combination is included in a corresponding document that is associated with the column-row combination, act 1902. In a very simple example, the document management application 214 creates a matrix with columns for 5 documents and rows for 9 words for a class of invoice documents, wherein the combination of the first column and the first row indicates that document 1 includes word 1.

Distances are identified between pairs of words, wherein each distance is based on a number of the documents that differ in including a corresponding pair of the words, act 1904. In a very simple example, the document management application 214 identifies the distance between word 2 and word 3 as 1 because all of the 5 documents include word 2 while 4 of the 5 documents include word 3. The document management application 214 may not have to compute the distances between every pair of words in the whole matrix because the clustering algorithm may use the distance function as needed.

Word clusters are created, wherein each word cluster includes pairs of words associated with a corresponding distance less than a distance threshold, act 1906. In a very simple example, the document management application 214 creates cluster 2 to include word 4, word 5, and word 9 because the distances between each of the words in cluster 2 are less than a distance threshold of 2.

Sets of word clusters are created, wherein a set of word clusters includes word clusters that are not associated with any of the documents associated with other word clusters in the set, act 1908. In a very simple example, the document management application 214 creates cluster set 2 to include cluster 2 and cluster 3 because documents 1, 3, and 5 that are associated with cluster 2 are not included in the documents 2 and 4 that are associated with cluster 3.

Subgroups of the digitized documents are created based on a set of word clusters with a highest word score, act 1910. In a very simple example, the document management application 214 divides the documents into 2 subgroups, subgroup 1 for documents 1, 3, and 5, and subgroup 2 for documents 2 and 4, because cluster set 2 includes 5 words, which is more than the number of keywords included in cluster set 1 or cluster set 3. As a result, the document management application 214 may group documents 1, 3, and 5 together as first pages of invoices and group documents 2 and 4 together as last pages of multi-paged invoices.

Although FIG. 19 depicts the acts 1902-1910 occurring in a specific order, the acts 1902-1910 may occur in another order. Embodiments herein enable creating subgroups of documents using optical character recognition data. This document management distinguishes pages by their content rather than their overall "look," resulting in a better subdivision of documents and higher recognition accuracy.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

Preferred embodiments are described herein, including the best mode known to the inventor for carrying out the claimed subject matter. Of course, variations of those preferred embodiments will become apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

What is claimed is:

1. A system for creating subgroups of documents using optical character recognition data, the system comprising:
   one or more processors; and
   a non-transitory computer readable medium storing a plurality of instructions, which when executed, cause the one or more processors to:
      create a matrix for words included in documents, wherein each column-row combination in the matrix indicates whether a corresponding word that is associated with the column-row combination is included in a corresponding document that is associated with the column-row combination;
      identify distances between pairs of the words in the matrix, wherein each distance is based on a number of the documents that differ in including a corresponding pair of the words;
      create word clusters, wherein each word cluster comprises pairs of words associated with a corresponding distance less than a distance threshold;
      create sets of word clusters, wherein a set of word clusters comprises word clusters that are not associated with any of the documents associated with other word clusters in the set of word clusters; and
      create subgroups of the digitized documents based on a set of word clusters corresponding to a high word score relative to at least one other word score corresponding to at least one other set of word clusters.

2. The system of claim 1, wherein the words comprise keywords associated with the documents based on a comparison of the documents with at least one of a class and a template.

3. The system of claim 1, wherein the documents comprise digitized optical character recognition data.

4. The system of claim 1, wherein the documents are associated with a class in response to a comparison to classify documents similar to a first document of the documents.

5. The system of claim 1, wherein the documents are associated with a template in response to a comparison to classify documents similar to a first document of the documents.

6. The system of claim 1, wherein the highest word score is based on a total number of words in the set of word clusters.

7. The system of claim 1, wherein the highest word score is based on an average number of words in the set of word clusters.

8. A computer-implemented method for creating subgroups of documents using optical character recognition data, the method comprising:
   creating a matrix for words included in documents, wherein each column-row combination in the matrix indicates whether a corresponding word that is associated with the column-row combination is included in a corresponding document that is associated with the column-row combination;
   identifying distances between pairs of the words in the matrix, wherein each distance is based on a number of the documents that differ in including a corresponding pair of the words;
   creating word clusters, wherein each word cluster comprises pairs of words associated with a corresponding distance less than a distance threshold;
   creating sets of word clusters, wherein a set of word clusters comprises word clusters that are not associated with any of the documents associated with other word clusters in the set of word clusters; and
   creating subgroups of the digitized documents based on a set of word clusters corresponding to a high word score relative to at least one other word score corresponding to at least one other set of word clusters.

9. The computer-implemented method of claim 8, wherein the words comprise keywords associated with the documents based on a comparison of the documents with at least one of a class and a template.

10. The computer-implemented method of claim 8, wherein the documents comprise digitized optical character recognition data.

11. The computer-implemented method of claim 8, wherein the documents are associated with a class in response to a comparison to classify documents similar to a first document of the documents.

12. The computer-implemented method of claim 8, wherein the documents are associated with a template in response to a comparison to classify documents similar to a first document of the documents.

13. The computer-implemented method of claim 8, wherein the highest word score is based on a total number of words in the set of word clusters.

14. The computer-implemented method of claim 8, wherein the highest word score is based on an average number of words in the set of word clusters.

15. A computer program product, comprising computer-readable program code to be executed by one or more processors when retrieved from a non-transitory computer-readable medium, the program code including instructions to:
   create a matrix for words included in documents, wherein each column-row combination in the matrix indicates whether a corresponding word that is associated with the column-row combination is included in a corresponding document that is associated with the column-row combination;
   identify distances between pairs of the words in the matrix, wherein each distance is based on a number of the documents that differ in including a corresponding pair of the words;
   create word clusters, wherein each word cluster comprises pairs of words associated with a corresponding distance less than a distance threshold;
   create sets of word clusters, wherein a set of word clusters comprises word clusters that are not associated with any of the documents associated with other word clusters in the set of word clusters; and create subgroups of the digitized documents based on a set of word clusters corresponding to a high word score relative to at least one other word score corresponding to at least one other set of word clusters.

16. The computer program product of claim 15, wherein the words comprise keywords associated with the documents based on a comparison of the documents with at least one of a class and a template.

17. The computer program product of claim 15, wherein the documents comprise digitized optical character recognition data.

18. The computer program product of claim 15, wherein the documents are associated with a class in response to a comparison to classify documents similar to a first document of the documents.

19. The computer program product of claim 15, wherein the documents are associated with a template in response to a comparison to classify documents similar to a first document of the documents.

20. The computer program product of claim 15, wherein the highest word score is based on a total number of words in the set of word clusters.

\* \* \* \* \*